(12) United States Patent
Bini

(10) Patent No.: US 11,471,130 B2
(45) Date of Patent: Oct. 18, 2022

(54) METHOD AND ULTRASOUND SYSTEM FOR SHEAR WAVE ELASTICITY IMAGING

(71) Applicant: ESAOTE SpA, Genoa (IT)

(72) Inventor: Giovanni Bini, Genoa (IT)

(73) Assignee: Esaote S.p.A., Genoa (IT)

( * ) Notice: Subject to any disclaimer, the term of this patent is extended or adjusted under 35 U.S.C. 154(b) by 589 days.

(21) Appl. No.: 16/408,789

(22) Filed: May 10, 2019

(65) Prior Publication Data

US 2019/0350559 A1    Nov. 21, 2019

(30) Foreign Application Priority Data

May 16, 2018    (EP) ..................... 18172549

(51) Int. Cl.
*A61B 8/08* (2006.01)
*A61B 8/00* (2006.01)
*G01S 7/52* (2006.01)

(52) U.S. Cl.
CPC ............ *A61B 8/5246* (2013.01); *A61B 8/469* (2013.01); *A61B 8/485* (2013.01); *G01S 7/5202* (2013.01);
(Continued)

(58) Field of Classification Search
CPC ............. G01S 7/52042; G01S 7/52022; G01S 7/5202; A61B 8/485; A61B 8/5246;
(Continued)

(56) References Cited

U.S. PATENT DOCUMENTS 5,606,971 A    3/1997  Sarvazyan
6,113,543 A *  9/2000  Bonnefous ......... A61B 5/02007
                                                600/438

(Continued)

FOREIGN PATENT DOCUMENTS

EP              3263036 A1      1/2018
WO     WO-2016108178 A1 *      7/2016 ............. A61B 8/485
WO         20170160783 A1      9/2017

OTHER PUBLICATIONS

European Search Report dated Aug. 30, 2018, which issued in corresponding European Patent Application No. EP 18 17 2549.

*Primary Examiner* — Amelie R Davis
*Assistant Examiner* — John Denny Li
(74) *Attorney, Agent, or Firm* — Dickinson Wright PLLC

(57) ABSTRACT

System and method for shear wave elasticity imaging perform
 a) acquiring B-mode ultrasound images of a target region;
 b) selecting a region of interest;
 c) transmitting a shear wave excitation pulse;
 d) measuring displacements of tracking focal points or depth ranges at different depths positions along each of laterally staggered tracking lines within the selected region of interest;
 e) determining a curve representing displacement of tissue as a function of time at different spatial locations within the region of interest;
 f) determining for spatial locations candidate time(s) of arrival of the shear wave at the spatial location as a function of the curve;
 g) finding linear functional relation between the time of arrival and the spatial coordinate in the lateral direction using Random Sample Consensus (RANSAC) algorithm; and
 h) determining the inverse of velocity of the shear wave in a spatial location as the angular coefficient of the linear function.

15 Claims, 13 Drawing Sheets

(52) U.S. Cl.
CPC ............... *G01S 7/52042* (2013.01); *G01N 2291/02475* (2013.01); *G01N 2291/02827* (2013.01)

(58) Field of Classification Search
CPC ......... A61B 8/469; G01N 2291/02475; G01N 2291/02827
See application file for complete search history.

(56) References Cited

U.S. PATENT DOCUMENTS

| | | |
|---|---|---|
| 8,137,272 B2 | 3/2012 | Cooley et al. |
| 2002/0010398 A1 | 1/2002 | Bonnefous |
| 2017/0156700 A1* | 6/2017 | Honjo ................ G01S 7/52042 |
| 2017/0340310 A1 | 11/2017 | Carlini et al. |
| 2018/0153516 A1* | 6/2018 | Labyed ............... G01S 15/8977 |

* cited by examiner

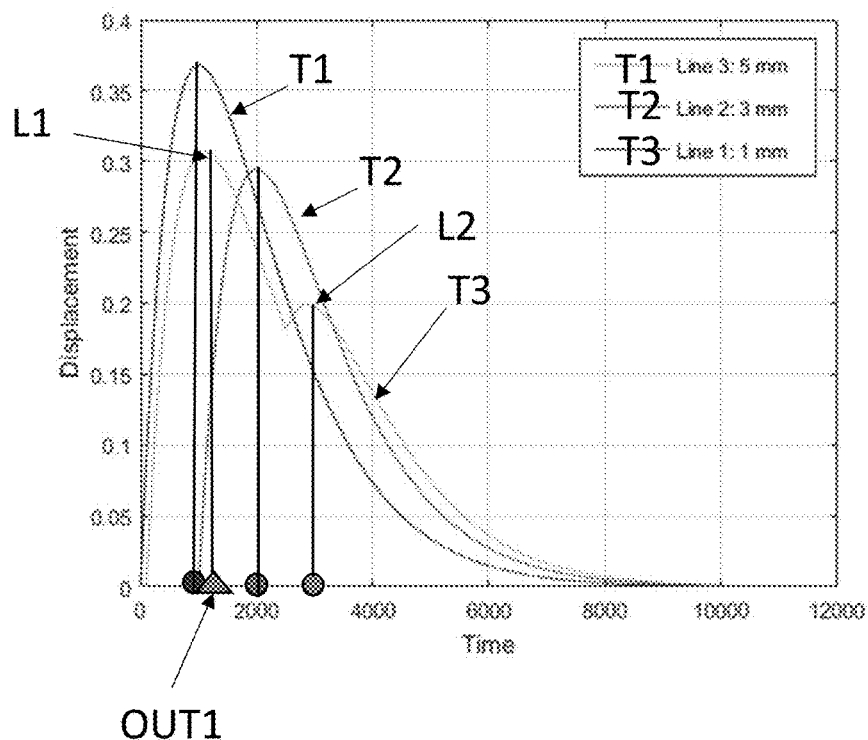
Figure 3A
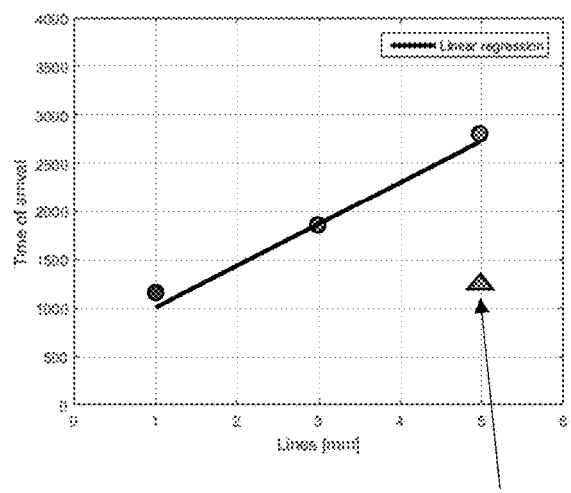
Figure 3B  OUT1
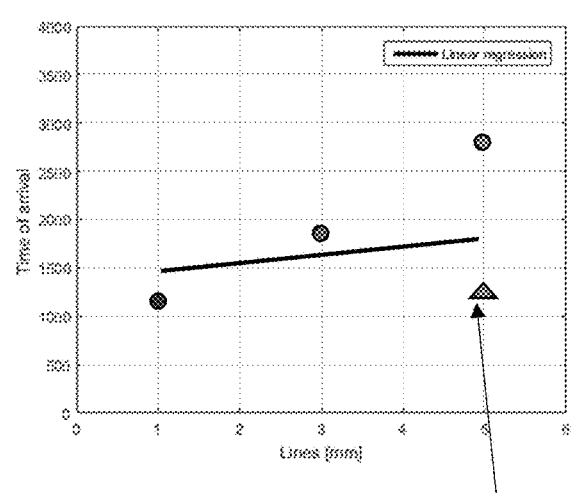
Figure 3C  OUT1

Point SW Time of start of the shear wave propagation at the spatial location of the excitation pulse considered as an additional point of calculating the rgression line

METHOD AND ULTRASOUND SYSTEM FOR SHEAR WAVE ELASTICITY IMAGING

BACKGROUND

Elasticity of soft biological tissues has been used for evaluating possible pathological conditions since the dawning of medicine. The use of manual palpations for evaluating the health condition of the tissues is still used commonly in routine medical examinations. For example, the presence of rigid masses found during routine breast examinations is often an early indication of breast cancer. Manual palpation methods however are relatively subjective and are limited to surface anatomical structures.

The methods for quantifying the elasticity or for the comparative measurement of biological tissues by ultrasounds allow deep-tissue elasticity to be measured in the body under examination, are reliable and therefore are used in clinical practice.

Unlike the traditional ultrasound imaging, such as, for example, B-mode, that allows images to be acquired where tissues with different acoustic properties are distinguished, the methods measuring the elasticity allow tissues with different mechanical properties to be distinguished. To do this, such methods carry out an excitation of the tissues and monitor the strain response, which is related to tissue elasticity.

Some elasticity measurement methods use transverse waves, or shear waves, generated after an excitation, and are defined as Shear Wave Elasticity Imaging (SWEI). These methods generate shear waves in the tissue following an acoustic disturbance, called a shock disturbance, of the first excitation point applied by the ultrasound probe, and consequently monitor the shear waves in the regions of interest within an area along which the shear waves propagate. By measuring the displacements over time of the image or of the pixels of the image or of the pixels of a Line of Sight at a plurality of lateral positions separated by a known distance from the excitation source, it is possible to estimate the shear wave speed.

Monitoring the shear waves is carried out by tracking pulses transmitted in the region of interest. The corresponding reflected echoes measures the displacements of the tissues along the tracking lines at which the tracking pulses are focused.

The target region at which the excitation pulse of the shear wave is directed is in many cases outside the region of interest within which the monitoring of the shear waves propagation is carried out. More generally the area at which the shear wave is generated could also be an area placed in the region of interest. In this case there is the need of monitoring the displacements induced by the shear waves in the tissue also in the area at which the excitation has occurred. Furthermore, if an excitation pulse is directed to an area outside the region of interest in which the monitoring of the displacements caused by the propagation of the shear wave is carried out, due to an azimuthal translation of a further excitation pulse in relation to the previous ones, the said excitation pulse could overlap the region in which one or more tracking pulses of one of the shear wave caused by one of the said previous tracking pulses are transmitted.

Actually, the measurement is indirect since the method detects the propagation speed of the shear wave in a direction substantially orthogonal to the acoustic shock disturbance of the excitation point.

The relation between speed of such shear wave and the elasticity is approximate and it depends on some assumptions about the density of the tissue under examination.

The tissue elasticity is proportional to the propagation speed of the shear wave Vs, according to the following formula:

$$E \approx 3\rho V_s^2$$

wherein $\rho$ is the density of the tissue and it is assumed that $\rho=1$, namely that tissue density is unit quantity.

The document U.S. Pat. No. 5,606,971 describes a shear wave elastography (SWE) method, that uses a focused ultrasound transducer which induces shear waves in a tissue by sending modulated ultrasonic pulses. The shear wave of the frequency of the modulating signal is detected. The mechanical properties of tissues under examination are evaluated based on the measured values of speed and attenuation of shear waves.

In shear wave elastography, one or a time sequence of shear wave excitation pulses are transmitted to a body to be examined toward an excitation target region, which lies outside a selected Region of Interest (ROI) in which the measurement of the elasticity is aimed. The generated shear waves propagate away from the excitation target region or excitation focal point in a direction substantially perpendicular to the direction of transmission of the excitation pulses. The propagation in time of the shear wave is tracked by a series of tracking pulses interleaved to the excitation pulses of the shear waves. Due to the effect of the acoustic radiation force of the excitation pulses, the tissue in the excitation target region is displaced simultaneously establishing a shear wave. For each lateral position along the shear wave propagation direction which is a direction perpendicular to the excitation pulse, the tissue motion induced by the shear wave will be mainly in the same direction as the one caused by the excitation pulse. Tracking pulses along several laterally staggered focal lines passing through a selected ROI can monitor such dynamic response for selected positions and lead to determining a position-specific displacement waveform representing the magnitude of tissue movement as a function of time caused by the transit of the shear wave front. Such waveforms can be computed at multiple positions along the shear wave propagation path and are processed for determining the speed of the propagation of the shear wave. Several methods have been used for processing shear wave ultrasound tracking data such as, for example, Fourier transform for estimating shear wave phase velocity or shear wave amplitude peak-to-peak spatial and temporal calculations for determining shear wave propagation speed. The speed at which a shear wave propagates inside the tissue is determined by the shear modulus, shear viscosity, tissue density and shear wave frequency through some mechanical models. The stiffer the tissue is, the faster the waves move.

In an embodiment the excitation pulses of the shear waves are transmitted in a direction which is parallel to a depth direction inside a body to be examined, and the shear wave propagation direction is perpendicular to the said direction. The laterally staggered tracking pulses are also transmitted and received along focalisation lines which are parallel to the direction of propagation of the said excitation pulses. Since shear waves have a certain width in the direction of propagation of the excitation pulses and in the specific embodiment in the depth direction inside the body to be examined, tracking data is acquired at different positions having different ranges of depths along each tracking line. In one dimensional shear wave elastography imaging, the data at the different depth ranges (e.g., segments of the line of sight along which a tracking pulse is focused) and along each tracking line are averaged in order to reconstruct the waveform of the displacements as a function of time along each of the laterally staggered tracking lines in the depth dimension of a region of interest. An example of such method is disclosed in document EP3240484.

FIGS. 1A to 1C show a simplified diagram of a probe emitting tracking pulses focalized along three different lines of sight indicated by T1, T2 and T3 and a shear wave excitation pulse 10. The tracking pulses and the shear wave excitation pulse are generated by an ultrasound probe 20 comprising an array of electroacoustic transducers.

FIG. 1B shows the principle of the one-dimensional shear wave elastography for each tracking line the displacement curve as a function of time is indicated. The displacement curves as a function of time along the line of sight at which each tracking pulse is focused are obtained by averaging the displacement data measured at different ranges of depth, i.e. at different segments of predetermined length of the line of sight, so that for every line of sight only one displacement curve is determined.

The time of arrival of each shear wave at a certain location can be estimated from the maxima of the displacement curves carrying out a linear regression of the time of arrival of the shear wave at the maxima of the said displacement curves.

Ultrasound echoes reflect and received by the probe are cross correlated in time after beamforming in order to determine the displacement of the tissue caused by the passage of the shear wave and thus the displacement curves in FIG. 1B. The result of one-dimensional shear wave elasticity imaging is a unique velocity value for the shear wave in the region of interest and thus a unique value for each elasticity parameter of the tissue in the region of interest which can be calculated starting from the velocity of the shear wave.

FIG. 1C shows the ideal condition of the shear wave velocity estimation using linear regression.

The slope a of the regression line is the inverse of the velocity of propagation of the shear wave and the linear regression is carried out on the data pair of the determined time of arrivals of the peaks of the displacement curves in FIG. 1B and the position coordinate of the corresponding line of sight or tracking line T1, T2, T3 in the direction of propagation 11 of the shear wave or in a direction perpendicular to the line of sights or tracking lines T1, T2, T3.

An alternative shear wave elasticity imaging method is the so called two-dimensional (2D) shear wave elastography method. This method presents 2D quantitative shear elasticity maps of the tissue, which are clinically useful for both focal lesion detection and diffuse disease diagnosis. In this case, the positional data of different tracking focal points or different segments corresponding to a sequence of different depth ranges along each tracking line and having different depth positions along each tracking line are processed separately for each depth position or range. A waveform of the displacement in time is thus generated for every tracking line and for every tracking focal point or depth range at a different depth along the tracking lines. The said tracking focal points or depth ranges are inside the area defined by a selected ROI and within the global depth range corresponding to the width in the depth direction of the shear wave. In US2002/0010398 a technique according to the two-dimensional shear wave elastography imaging method is disclosed.

Differently from the one-dimensional case described above, in the two-dimensional case a different displacement curve over time is determined for each of the points or each of the depth ranges provided along each tracking line.

Also in this case a unique regression line may be determined by applying a regression algorithm for each depth range or for a combination of depth ranges.

According to an embodiment, in the two-dimensional case, a plurality of regression lines are determined for each depth in each one of these lines corresponding to a different sub-region identified by a different lateral coordinate, i.e. position.

Inhomogeneities of the tissue and the presence of interfaces between different kinds of adjacent tissues, and further also discrepancies of the reality with the theoretical model, may cause distortions of the measured displacement curves which determine spurious peaks as it is shown in FIGS. 3B and 3C. When these spurious peaks have an intensity or an energy which is higher relatively to the theoretically maxima peak caused by the shear wave passage, then the estimated or calculated time of arrival of the shear wave may cause outliers in the coordinates of the maximum peak or in the cross correlation process with an expected shape of the displacement curve. This situation is illustrated in FIGS. 3B and 3C in which the point OUT1 represents the outlier. The said outliers influence the estimation by means of a linear regression algorithm rendering these estimations unreliable.

As it is disclosed also in document EP3240484, shear wave elastography imaging is carried out in parallel or interleaved with ultrasound morphologic imaging, so called B-mode imaging reproducing the anatomy of an area of the object to be examined. The shear wave elastography imaging is then applied to a selected sub-area, a so-called Region of Interest (ROI) of the B-mode imaged area. The anatomic images allow identifying one or more specific ROI in which shear wave elastography imaging must be carried out.

SUMMARY

An object of the present disclosure consists in providing a method and a system allowing more precise estimation of the velocity and/or other elasticity parameter of the tissue in an imaged ROI.

A further object comprises improving the fitness of the estimated elasticity parameters by overcoming the problem of the so-called outliers, thereby obtaining more reliable results of the estimation.

Still a further object comprises improving the resolution of the estimated time of arrivals and the related shear wave velocity data and the other elasticity parameters by obtaining estimation data for sub regions of the selected region of interest.

Another object comprises providing a more precise and direct visual representation for the doctors of the determined elastic parameters.

Another object comprises visually differentiating the different parameters which describe the elastic properties of the tissue in the ROI subjected to shear wave elastography imaging, allowing the doctor to directly appreciate the conditions at a certain structure within the tissue imaged and thereby furnishing a more effective and intuitive aid to the diagnosis.

According to a first embodiment herein a method for shear wave elasticity imaging is provided comprising:

a) acquiring B-mode ultrasound images of a target region in a body under examination;

b) selecting a region of interest inside the said B-mode image;

c) transmitting a shear wave excitation pulse focalized on an excitation region;

d) measuring the displacements of a certain number of tracking focal points or depth ranges at different depths positions along each one of a predefined number of laterally staggered tracking lines within the selected region of interest;

e) determining a curve representing the displacement of the tissue as a function of time at different spatial locations within the region of interest;

f) determining for each said spatial locations in the region of interest one or multiple candidate times of arrival of the shear wave at the said spatial location as a function of the curve determined at point e);

g) finding the linear functional relation between the said candidate times of arrival and the spatial coordinate in the said lateral direction, i.e. in the direction of propagation of the shear wave perpendicular to the direction of the tracking lines, which linear function best approximates the determined time of arrivals at the positions of the tracking lines along the said lateral direction;

h) determining the inverse of the velocity of the shear wave in a spatial location as the angular coefficient of the said linear function in a coordinate system representing the time of arrival along the y-coordinate and the position along the lateral direction at which the time of arrival has been recorded on the x-coordinate, i.e. the slope of the straight line representing the said linear function in the said coordinate system, wherein operation g) comprises determining the linear function best fitting the said candidate times of arrival applying a Random Sample Consensus algorithms (RANSAC algorithm).

The candidate times of arrival of the shear wave at the different spatial coordinates or locations may be determined using different algorithms.

According to one embodiment, one candidate time of arrival of the shear wave for each different spatial coordinate or location may be determined by setting as the time of arrival of the shear wave the time of the peak of the displacement curve at the corresponding spatial location.

According to a variant embodiment, multiple candidate times of arrival of the shear wave for each different spatial coordinate or location may be determined by setting as the times of arrival of the shear wave the times of the local maxima of the displacement curve at the corresponding spatial location.

According to a variant embodiment, the one candidate time of arrival of the shear wave for each different spatial coordinate or location is determined by setting the said time of arrival of the shear wave at the different spatial coordinates using the peak of the cross-correlation between the measured displacement curve at a spatial location and a reference displacement curve. The reference displacement curve may be obtained by measuring a displacement curve at a reference lateral position oir coordinate (absolute time of peak) or at the position of the line of sight which is laterally adjacent to the line of sight at which the time of arrival is to be determined (relative time of peak).

According to a variant embodiment, the multiple candidate times of arrival of the shear wave for each different spatial coordinate or location is determined by setting the said times of arrival of the shear wave at the different spatial coordinates using the local maxima of the cross-correlation between the measured displacement curve at a spatial location and a reference displacement curve. The reference displacement curve may be obtained by measuring a displacement curve at a reference lateral position oir coordinate (absolute time of peak) or at the position of the line of sight which is laterally adjacent to the line of sight at which the time of arrival is to be determined (relative time of peak).

According to an embodiment, the reference curve may be a synthetic one obtained from theory or by simulations.

In the above method steps the RANSAC algorithm calculates every possible regression line and choses as the best fit the regression line for which the number of outliers is a minimum. The outliers are the data whose distance to the fitting line is higher than a predefined threshold.

According to an embodiment provided in combination with one or more of the above embodiments, a further criterion for choosing the regression line representing the best fit consists in choosing the regression line for which the sum of the quadratic error related to the inliers is minimum. The inliers are the data whose distance to the fitting line is lower than a predefined threshold.

According to an embodiment, the spatial locations at which the time of arrival of the local maxima are determined are tracking points or depth ranges positioned at different depth on at least part or on each of the tracking lines crossing the region of interest.

According to an embodiment related to the so called one dimensional shear wave elasticity imaging, the displacement curve as a function of time related to a tracking line, i.e. at the corresponding lateral position of the said tracking line relatively to the other tracking lines in the said lateral direction is the average of the measured displacements at a plurality of tracking points on the said tracking line having different depths or at a plurality of depth ranges along the said tracking line having different depths.

According to a variant embodiment related to the so called two-dimensional elasticity imaging, the velocity of the shear wave is determined separately at least at two different depths of the region of interest by determining carrying out the steps a) to j) separately for each of the said two depths.

In an embodiment for each of the said two depths the displacement curves are determined at tracking points or at depth ranges positioned on the tracking lines at the said at least two depths or representative of the said depths, the steps a) to j) being carried out independently for the displacement curves as a function of time determined at the tracking line positions at each one of the said at least two depths.

This variant embodiment can be provided also in combination with one or more of the above disclosed variants, particularly relating to the criteria of choosing the best linear regression of the data pairs displacement and time of arrival at the said at least two depths or depths ranges, the data pairs relating to candidate times of arrival and corresponding lateral positions in the step g).

In relation to the term tracking point and range depth is important to stress out that the two definitions are to be considered comprising each other.

Indeed the tracking pulses along a tracking line may be focalized not on a single point but on a certain segment of the tracking line having a certain length and positioned at a certain depth along the tracking line, or the displacement data of a certain number of tracking points on a tracking line having different depths may be averaged and the averaged displacement data, i.e. the averaged displacement curve as a function of time is chosen to representative of a depth range centred on a central tracking point of the said certain number of tracking points or on a central point of the said depth range.

According to a further embodiment which can be provided alternatively or in combination with one or more of the above embodiments, a method for shear wave elasticity imaging is provided comprising:

a) acquiring B-mode ultrasound images of a target region in a body under examination;

b) selecting a region of interest inside the said B-mode image;

c) transmitting a shear wave excitation pulse focalized on an excitation region;

d) measuring the displacements of a certain number of tracking focal points or depth ranges at different depths positions along each one of a predefined number of laterally staggered tracking lines within the selected region of interest;

e) determining a curve representing the displacement of the tissue as a function of time at different spatial locations within the region of interest;

f) determining for each said spatial locations in the region of interest the one or multiple candidate times of arrival of the shear wave at the said spatial location. The one candidate time of arrival is set either as the time of the peak of the displacement curve at the corresponding spatial location or the time of peak of the cross correlation of the measured displacement curve at the said spatila location with a reference displacement curve measured at a reference spatial location; the multiple candidate times of arrival are set either as the times of the local maxima of the displacement curve at the corresponding spatial location or the times of the local maxima of the cross correlation of the measured displacement curve at the said spatial location with a reference displacement.

g) finding the linear functional relation between the candidate times of arrival and the spatial coordinate in the said lateral direction, i.e. in the direction of propagation of the shear wave perpendicular to the direction of the tracking lines, which linear function best approximates the determined time of arrivals at the positions of the tracking lines along the said lateral direction;

h) determine the inverse of the velocity of the shear wave in a spatial location as the angular coefficient of the said linear function in a coordinate system representing the candidate times of arrival along the y-coordinate and the position along the lateral direction at which the time of arrival has been recorded on the x-coordinate, i.e. the slope of the straight line representing the said linear function in the said coordinate system, and in which method the steps are provided which are carried out at least before carrying out step g)

i) estimating at one or more of the spatial locations, i.e. at one or more of the lateral positions of the tracking lines the expected maximum and minimum values of the velocities of propagation of the shear wave at the said spatial locations;

j) mapping the said values on the coordinate system representing the data pairs relating to the candidate times of arrival and the corresponding position in the lateral direction, i.e. the position of the corresponding tracking line;

k) not considering for the execution of step g) the data pairs relating to candidate times of arrival and positions of the corresponding tracking line corresponding to shear wave velocities which are higher than the maximum velocity or lower than the minimum velocity estimated in steps i) and j) at the position of the corresponding tracking line.

According to an embodiment there is provided the step of determining the velocity of the shear wave at a certain spatial location by considering the time of start of the shear wave propagation in the lateral direction, this time being determined theoretically.

According to still another embodiment, the said time of start of the shear wave propagation is added to the data pairs relating to candidate times of arrival and lateral position on which the step g is carried out.

According to a variant embodiment the data defining the time of start of the shear wave propagation is weighted in such a way as to have a higher weight than the other data on which step g) is applied.

Also in relation to the above embodiments related to estimating expected minimum and maximum velocity of propagation of the shear waves and filtering out the measured data corresponding to shear wave velocities which are outside the field delimited by the said minimum and maximum thresholds, the method can be applied alternatively by averaging over the tracking points at the different depth along the tracking lines or over the different depth ranges along the tracking lines in a one dimensional shear wave elasticity imaging configuration or by executing the above disclosed steps independently for at least two different depths within the region of interest similarly as already disclosed above for the configuration of the method according to a two dimensional shear wave elasticity imaging.

According to an embodiment, the velocity of the shear wave propagation can serve as a basis for calculating elasticity parameters including one or more of the parameters of the group comprising: velocity of the shear wave propagation, Young's modulus, shear modulus, bulk modulus, Poisson's ratio, Lamè's first parameter, P-wave and combinations of these parameters. This meaning of the term elasticity parameter applies for the description and for the claims.

According to still a further embodiment which can be provided in any combination with the one or more preceding embodiments, the method comprises the steps of:

measuring the displacements of a certain number of tracking focal points at different depths positions or at different depths ranges along each one of a predefined number of laterally staggered tracking lines within the selected region of interest;

determining the elasticity parameters of the regions between at least two of the said tracking focal points at the same depth and on at least two adjacent tracking lines as a function of the displacements caused by the shear wave at the said tracking focal points.

A further embodiment which can be provided in combination with any of the embodiments and variants described before comprises the steps of modifying the appearance of at least one pixel of the B-mode image inside the region of interest and for which the velocity of the shear wave propagation and/or other elasticity parameters has been determined relatively to the grey-scale B-mode image as a function of at least one of the elasticity parameters determined for the said at least one pixel and displaying the said at least one pixel with a modified appearance at the corresponding pixel of the B-mode image.

In relation to the two-dimensional shear wave elasticity imaging, the distance of the tracking focal points or of the depths ranges along each tracking line and the distance of the tracking lines determine the highest resolution which may extend over only one pixel or over a group of pixels representing a sub area of the region of interest.

The tracking of the shear wave propagation in the region of interest can be carried out according to several methods.

According to a first embodiment the tracking can be carried out by acquiring the ultrasound signals along each one of a certain number of selected tracking lines by focusing a tracking ultrasound pulse along each tracking line and at one or more tracking points at different depths along said line and receiving the reflected signals along the said tracking line from each tracking point at the different depths. The acquisition is carried out one line after the other.

According to a further embodiment the tracking can be carried out by applying a so called multiline technique such as for example a so-called RTB-beamforming (Retrospective Transmit Beamforming). Examples of this method are disclosed in U.S. Pat. No. 8,137,272 and in EP3263036 of the same applicant.

According to still a further embodiment, the tracking of the shear wave can be carried out by using a method in which an unfocused plane wave is transmitted into the region of interest and beamforming is carried out during the signal reception phase according to a backpropagation scheme or according to standard delay and sum beamforming in reception.

In combination with the above mentioned alternative embodiments, for the method of carrying out the shear wave propagation tracking data acquisition several further acquisition techniques known in the art can be used.

The present disclosure relates also to a method for quantifying the elasticity of a material by ultrasounds comprising:

a) acquiring an ultrasound image;
b) defining a region of interest in the image;
c) defining an excitation region or point in the acquired image;
d) generating at least one acoustic excitation ultrasound pulse and transmitting the said excitation ultrasound pulse focalized at the said excitation region or point, for generating at least one shear wave, which shear wave originates in the first excitation point and has a direction of propagation substantially perpendicular to the direction of propagation of the ultrasound excitation pulse, the said excitation region or point being positioned in such a manner that the shear wave passes through the region of interest;
e) measuring the displacements induced by the shear wave at predefined tracking focal points in the region of interest at a plurality of tracking lines of sight passing through the region of interest and at different predetermined laterally staggered distances from the excitation region or point and within a predefined depth range along each tracking line;
f) calculating the speed of the measured shear wave using the said displacement data at the said tracking focal points;
g) assessing, by calculation, elasticity parameter values of the material in the region of interest based on the measured speed of the shear wave.

According to an embodiment, step g) is carried out by applying the following steps:

g1) defining sub-regions of the region of interest which sub regions are delimited laterally by two of the tracking lines and in the direction of depth by depth ranges coinciding with at least one tracking point having a certain depth position on each of the said two tracking lines and which at least one point or depth range on the first of the said tracking line having equal depth as the corresponding at least one tracking point or depth range on the second tracking line;

g2) the said two tracking lines and the said depth ranges being directly adjacent one to the other or one or more tracking line and/or one or more tracking points or depth ranges being provided between the said two tracking lines and the said two tracking points or depth ranges;

g3) calculating the speed of the shear wave in each of the said sub-regions of the region of interest using the displacement data at each tracking point or depth range on each tracking line delimiting and/or being within the said sub-region;

g4) assessing, by calculation, an elasticity parameter of the material in each of the sub-regions of the region of interest based on the measured speed of the shear wave.

The material in question can be of any type, both non-biological type, as in the case of non-destructive testing, and composed of biological tissues.

According to an embodiment an ultrasound system is provided for shear wave elasticity imaging (SWEI) comprising:

An ultrasound probe;

An ultrasound image acquisition section configured to acquire at least ultrasound anatomic images such as B-mode images;

A shear wave excitation pulse generation unit for transmitting said shear wave excitation pulses at a shear wave excitation region or point in a target region;

an ultrasound shear wave tracking section configured to transmit and receive ultrasound tracking beams in a selected region of interest;

A processing unit of the ultrasound received tracking beams, which unit is configured to calculate elasticity parameter values in the selected region of interest according to the steps defined in one or more of the preceding embodiments or variants.

According to an embodiment, the ultrasound system comprises an ultrasound probe;

An ultrasound transmit-wave generator and an ultrasound transmit beamformer;

An ultrasound receive-beamformer;

ultrasound receive signals processing unit for generating ultrasound image data;

a shear wave excitation pulse generator and a shear wave beamformer;

a central control unit comprising:

a memory storing program instructions;

at least one processor that executes the program instructions to:

define a region of interest in the ultrasound image;

generate an acoustic excitation ultrasound pulse directed at an excitation region or point, the said acoustic excitation ultrasound pulse being configured to produce a shear wave that has a direction of propagation extending laterally from a direction of propagation of the acoustic excitation ultrasound pulse, i.e. along a direction perpendicular to the direction of transmission of the ultrasound excitation pulse;

generate ultrasound tracking beams focused along different tracking lines which are at different predetermined laterally staggered distances one from the other and from the said excitation region or point;

process the ultrasound echo signal reflected at different tracking focal points distributed along the said tracking lines for calculating the values of elasticity parameters in the region of interest;

representing the elasticity parameter value distribution in the region of interest by means of an elasticity image the appearance of the pixels of the said elasticity image being determined as a function of the said elasticity parameter;

the said program instructions comprising the instructions to configure the processing unit to carry out the steps according to one or more of the embodiments of the method described above.

According to a further embodiment, there's an ultrasound system for shear wave elasticity imaging (SWEI) comprising:

an ultrasound probe;

an ultrasound transmit-wave generator and an ultrasound transmit beamformer;

an ultrasound receive-beamformer;

ultrasound receive signals processing unit for generating ultrasound image data;

a shear wave excitation pulse generator and a shear wave beamformer;

a display;

a central control unit comprising:

a memory storing program instructions;

at least one processor that executes the program instructions to:

define a region of interest in the ultrasound image;

generate an acoustic excitation ultrasound pulse directed at an excitation region or point, the said acoustic excitation ultrasound pulse being configured to produce a shear wave that has a direction of propagation extending laterally from a direction of propagation of the acoustic excitation ultrasound pulse, i.e. along a direction perpendicular to the direction of transmission of the ultrasound excitation pulse;

generate ultrasound tracking beams focused along different tracking lines which are at different predetermined laterally staggered distances one from the other and from the said excitation region or point;

process the ultrasound echo signal reflected at different tracking focal points distributed along the said tracking lines for calculating the values of elasticity parameters in the region of interest by:

a) measuring the displacements of a certain number of tracking focal points or depth ranges at different depths positions along each one of a predefined number of laterally staggered tracking lines within the selected region of interest;

b) determining a curve representing the displacement of the tissue as a function of time at different spatial locations within the region of interest;

c) determining for each said spatial locations in the region of interest one or multiple candidate times of arrival of the shear wave at the said spatial location. The one candidate time of arrival is set either as the time of the peak of the displacement curve at the corresponding spatial location or the time of peak of the cross correlation of the measured displacement curve at the said spatial location with a reference displacement curve measured at a reference spatial location or determined from theoretical calculations or simulations; the multiple candidate times of arrival are set either as the times of the local maxima of the displacement curve or the times of the local maxima of the cross correlation of the measured displacement curve at the said spatial location with a reference displacement curve measured at a reference spatial location or determined from theoretical calculations or simulations;

d) finding the linear functional relation between the candidate times of arrival and the spatial coordinate in the said lateral direction, i.e. in the direction of propagation of the shear wave perpendicular to the direction of the tracking lines, which linear function best approximates the determined time of arrivals at the positions of the tracking lines along the said lateral direction;

e) determining the inverse of the velocity of the shear wave in a spatial location as the angular coefficient of the said linear function in a coordinate system representing the time of arrival along the y-coordinate and the position along the lateral direction at which the time of arrival has been recorded on the x-coordinate, i.e. the slope of the straight line representing the said linear function in the said coordinate system, wherein operation d) comprises determining the linear function best fitting the said candidate times of arrival applying a Random Sample Consensus algorithm (RANSAC algorithm), the display configured to represent the elasticity parameters and/or velocity parameters value distribution in the region of interest by means of an elasticity image, the appearance of the pixels of the said elasticity image being determined as a function of the said elasticity parameter.

Embodiments herein also relate to an ultrasound system for shear wave elasticity imaging (SWEI) comprising:

an ultrasound probe;

an ultrasound transmit-wave generator and an ultrasound transmit beamformer;

an ultrasound receive-beamformer;

ultrasound receive signals processing unit for generating ultrasound image data;

a shear wave excitation pulse generator and a shear wave beamformer;

a display;

a central control unit comprising:

a memory storing program instructions;

at least one processor that executes the program instructions to:

define a region of interest in the ultrasound image;

generate an acoustic excitation ultrasound pulse directed at an excitation region or point, the said acoustic excitation ultrasound pulse being configured to produce a shear wave that has a direction of propagation extending laterally from a direction of propagation of the acoustic excitation ultrasound pulse, i.e. along a direction perpendicular to the direction of transmission of the ultrasound excitation pulse;

generate ultrasound tracking beams focused along different tracking lines which are at different predetermined laterally staggered distances one from the other and from the said excitation region or point;

process the ultrasound echo signal reflected at different tracking focal points distributed along the said tracking lines for calculating the values of elasticity parameters in the region of interest by:

a) measuring the displacements of a certain number of tracking focal points or depth ranges at different depths positions along each one of a predefined number of laterally staggered tracking lines within the selected region of interest;

b) determining a curve representing the displacement of the tissue as a function of time at different spatial locations within the region of interest;

c) determining for each said spatial locations in the region of interest one or multiple candidate times of arrival of the shear wave at the said spatial location. The one candidate time of arrival is set either as the time of the peak of the displacement curve at the corresponding spatial location or the time of peak of the cross correlation of the measured displacement curve at the said spatial location with a reference displacement curve measured at a reference spatial location or determined from theoretical calculations or simulations; the multiple candidate times of arrival are set either as the times of the local maxima of the displacement curve or the times of the local maxima of the cross correlation of the measured displacement curve at the said spatial location with a reference displacement curve measured at a reference spatial location or determined from theoretical calculations or simulations;

d) finding the linear functional relation between the candidate times of arrival and the spatial coordinate in the said lateral direction, i.e. in the direction of propagation of the shear wave perpendicular to the direction of the tracking lines, which linear function best approximates the determined times of arrivals at the positions of the tracking lines along the said lateral direction;

e) determining the inverse of the velocity of the shear wave in a spatial location as the angular coefficient of the said linear function in a coordinate system representing the time of arrival along the y-coordinate and the position along the lateral direction at which the time of arrival has been recorded on the x-coordinate, i.e. the slope of the straight line representing the said linear function in the said coordinate system;

f) estimating at one or more of the spatial locations, i.e. at one or more of the lateral positions of the tracking lines the expected maximum and minimum values of the velocities of propagation of the shear wave at the said spatial locations;

g) mapping the said values on the coordinate system representing the data pairs relating to the candidate times of arrival and the corresponding position in the lateral direction, i.e. the position of the corresponding tracking line;

h) not considering for the execution of step d) the data pairs relating to candidate times of arrival and position of the corresponding tracking line corresponding to shear wave velocities which are higher than the maximum velocity or lower than the minimum velocity estimated in steps f) and g) at the position of the corresponding tracking line, the display configured to represent the elasticity parameters and/or velocity parameters value distribution in the region of interest by means of an elasticity image, the appearance of the pixels of the said elasticity image being determined as a function of the said elasticity parameter.

A further embodiment relates to an ultrasound system for shear wave elasticity imaging (SWEI) comprising:
an ultrasound probe;
an ultrasound transmit-wave generator and an ultrasound transmit beamformer;
an ultrasound receive-beamformer;
ultrasound receive signals processing unit for generating ultrasound image data;
a shear wave excitation pulse generator and a shear wave beamformer;
a display;
a central control unit comprising:
a memory storing program instructions;
at least one processor that executes the program instructions to:
define a region of interest in the ultrasound image;
generate an acoustic excitation ultrasound pulse directed at an excitation region or point, the said acoustic excitation ultrasound pulse being configured to produce a shear wave that has a direction of propagation extending laterally from a direction of propagation of the acoustic excitation ultrasound pulse, i.e. along a direction perpendicular to the direction of transmission of the ultrasound excitation pulse;
generate ultrasound tracking beams focused along different tracking lines which are at different predetermined laterally staggered distances one from the other and from the said excitation region or point;

process the ultrasound echo signal reflected at different tracking focal points distributed along the said tracking lines for calculating the values of elasticity parameters in the region of interest by:

a) measuring the displacements induced by the shear wave at predefined tracking focal points in the region of interest at a plurality of tracking lines of sight passing through the region of interest and at different predetermined laterally staggered distances from the excitation region or point and within a predefined depth range along each tracking line;

b) calculating the speed of the measured shear wave using the said displacement data at the said tracking focal points;

c) assessing, by calculation, elasticity parameter values of the material in the region of interest based on the measured speed of the shear wave, wherein step c) comprises:

c1) defining sub-regions of the region of interest which sub regions are delimited laterally by two of the tracking lines and in the direction of depth by depth ranges coinciding with at least one tracking point having a certain depth position on each of the said two tracking lines and which at least one point or depth range on the first of the said tracking line having equal depth as the corresponding at least one tracking point or depth range on the second tracking line;

c2) the said two tracking lines and the said depth ranges being directly adjacent one to the other or one or more tracking line and/or one or more tracking points or depth ranges being provided between the said two tracking lines and the said two tracking points or depth ranges;

c3) calculating the speed of the shear wave in each of the said sub-regions of the region of interest using the displacement data at each tracking point or depth range on each tracking line delimiting and/or being within the said sub-region;

c4) assessing, by calculation, an elasticity parameter of the material in each of the sub-regions of the region of interest based on the measured speed of the shear wave, the display configured to represent the elasticity parameters and/or velocity parameters value distribution in the region of interest by means of an elasticity image, the appearance of the pixels of the said elasticity image being determined as a function of the said elasticity parameter

BRIEF DESCRIPTION OF THE DRAWINGS

FIG. 3A represents the estimation of shear wave times of arrival by means of local maxima of the displacement curve, determining the generation of outliers in the data to which linear regression is applied.

FIG. 3B is the result of applying one embodiment of the method in which all the data relating to all the local maxima are considered and the regression line is calculated by using a RANSAC algorithm, the criteria of choosing the regression line which best fits the data being in this case the reduction of the number of the outliers.

FIG. 3C is a diagram analogous to the one of FIG. 3B in which the criterium of choosing the best fitting regression line is the one of the regression line minimizing the quadratic error of the inliers.

DETAILED DESCRIPTION OF ILLUSTRATIVE EMBODIMENTS

Figure 2:
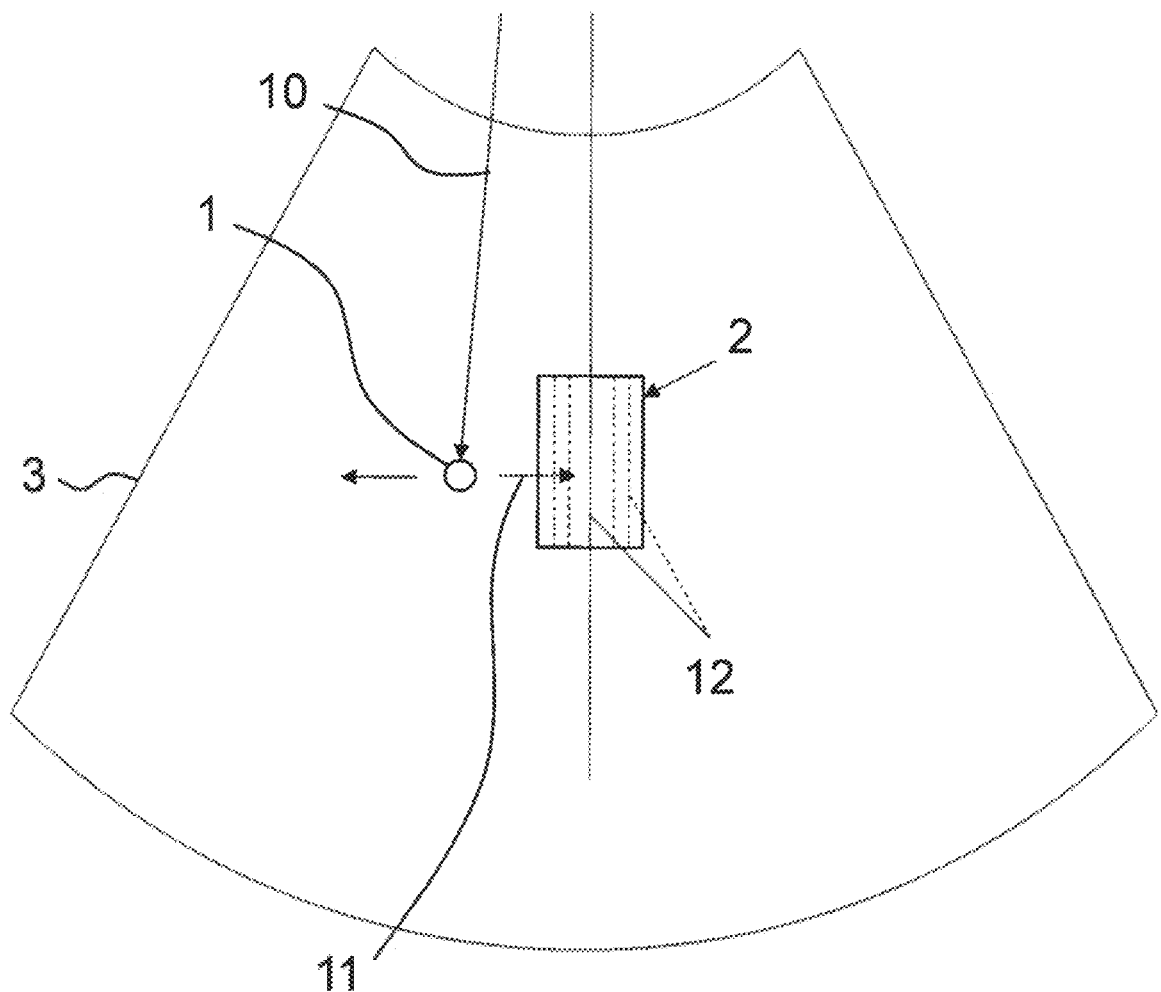
FIG. 2 is a simplified representation of an ultrasound image in which there is shown the region to which the shear wave excitation pulse is applied and the region of interest in which the shear wave propagation is tracked.

FIG. 2 shows an image representing schematically the operations of a method according to embodiments herein. An anatomic image of a target region 3 is acquired. On the B-mode image 3 the user defines a region of interest 2 through a gate, in which region of interest 2 the tissue elasticity is desired to be indirectly measured.

The region of interest 2 may have any shape, preferably a rectangular shape or as a section of an annulus, and preferably it has a predetermined size for the end user. The user can place the region of interest 2 where desired.

During the dedicated acquisition, the B-mode image is still, or "frozen", and it can be removed from such condition only after having performed the transmission-reception sequence along the tracking lines which is characteristic of shear wave elastography process.

Once having defined the region of interest 2, the shear wave elasticity imaging process starts. The elasticity parameters of the region of interest are determined by tracking the shear wave passage along the region of interest and as a function of the displacements caused by the shear wave propagation to the material, i.e. the tissue in the region of interest.

Once a measurement has ended, the image can be "unfrozen" such to allow a new shot and a new acquisition, until leaving the mode.

Once the region of interest 2 is defined, an excitation point or region 1 is defined within the acquired B-mode image 3. The excitation point or region 1 is placed outside the region of interest 2 and preferably laterally displaced relatively to the region of interest when referred to the direction of propagation of the tracking beams 12.

Therefore, a focused ultrasonic beam 10 is generated for acoustically generating an excitation pulse at point or region 1, to cause the generation of a shear wave 11. The shear wave 11 originates in the excitation point or region 1 and has a propagation direction substantially perpendicular to the direction of propagation of the ultrasonic excitation beam 10, in the two opposite departing directions denoted by the arrows shown in the FIG. 2. The excitation point 1 is placed such that the shear wave 11 passes through the region of interest 2. The generated shear wave 11 is measured at a plurality of lines of sight 12 which are focused such that they pass inside the region of interest 2 at different predetermined lateral distances from the said excitation point 1. FIG. 2 shows the line of sight under examination as a continuous line 12, while the other lines of sight are broken lines.

By the measurement of the passage of the shear wave on all the tracking lines or lines of sight 12, the propagation speed of the measured shear wave is calculated.

Figure 1A:
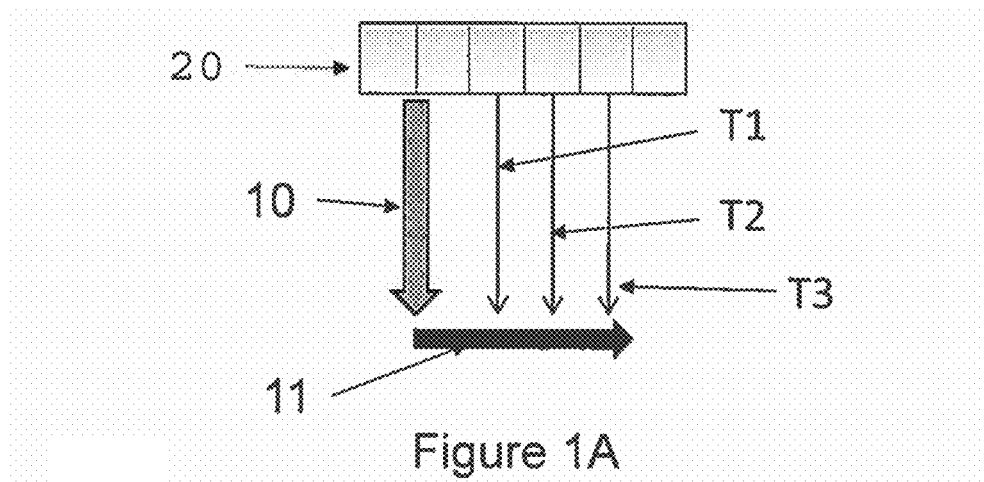
FIGS. 1A to 1C are diagrams representing in a simplified way a theoretical method of determining the velocity of the shear wave propagation in a region of interest according to the one-dimensional share wave elasticity imaging mode.
Figure 1B:
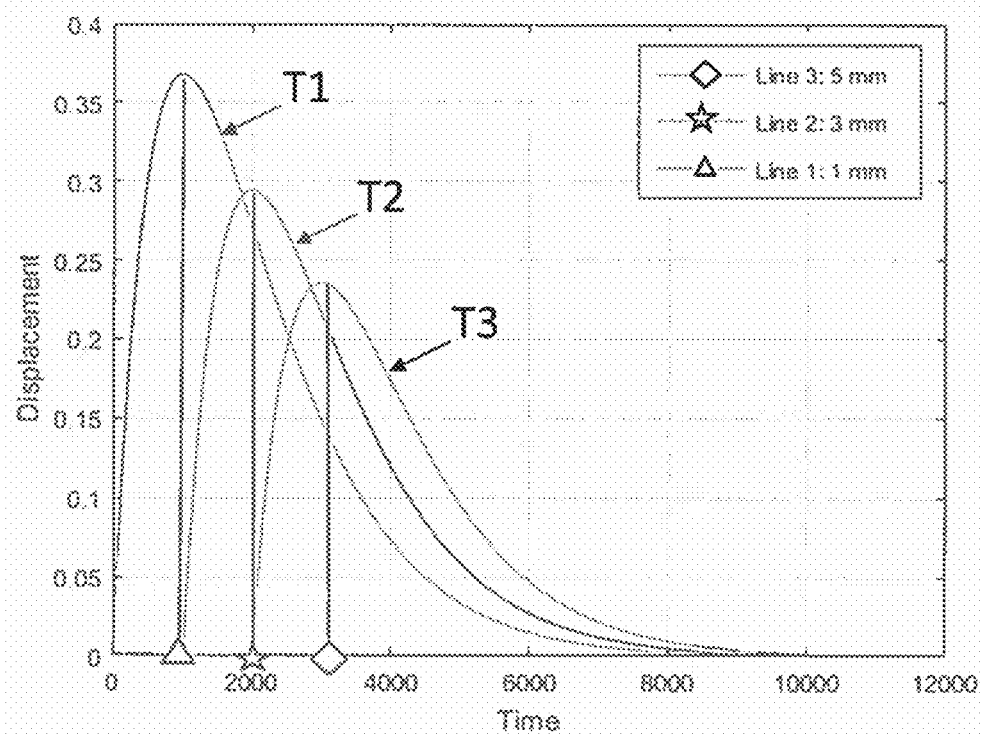
Figure 1C:
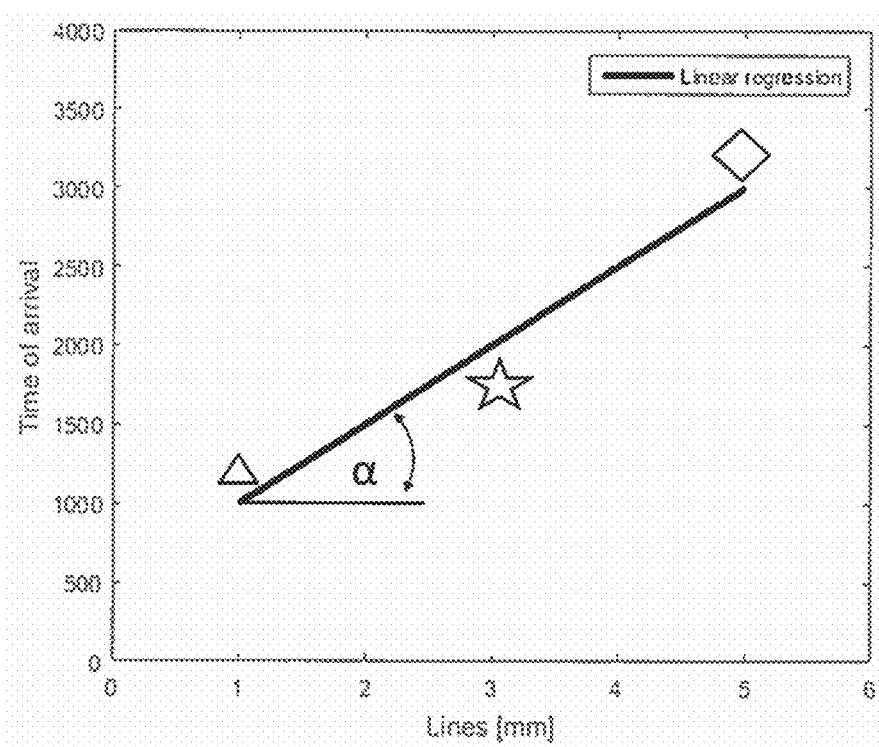

FIG. 3A shows an example of how the displacement curves as a function of time may appear in a real case in comparison to the theoretical case illustrated in FIG. 1B. The example is extremely simplified in order to better appreciate the technical principle.

As shown, the displacement curve as a function of time measured along the tracking line T3 shows a local maximum at L1 and at L2. The local maximum at L1 represents an outlier of the distribution of the data relating to the times of arrival as a function of the position of a tracking line and is indicated by OUT1.

Applying a traditional regression algorithm would lead to an imprecise determination of the velocity of the share wave propagation and of the elasticity parameters calculated from it.

A method according to embodiments herein considers each time relating to each of the local maxima in the displacement curve as a candidate time of arrival for finding a regression line. The best fitting regression line is determined by applying on the data pairs relating to the candidate times of arrival and corresponding position of the tracking line in the lateral direction a RANSAC algorithm.

This algorithm operates by calculating possible regression lines and then choosing the one considered to best fit the data applying at least one criteria or a combination of criteria.

FIGS. 3B and 3C show the result of the processing by the RANSAC algorithm by considering two different criteria respectively.

In FIG. 3B the criteria for determining the best regression line was to minimize the number of outliers. The regression line thus is close to three of four local times related to four local maxima of the three displacement curves.

The diagram of FIG. 3C shows the result when the criteria for choosing the best fitting regression line is set as the line minimizing the quadratic error on the data points.

According to an embodiment not shown in the figures, these two criteria could also be combined and optionally also differently weighted in their combination.

The RANSAC algorithm is per se known in the art a generic description of the algorithm can be found in Martin A. Fischer and Robert C. Bolles SRI International, Random Sample consensus: A Paradigm for Model Fitting with Applications to Image Analysis and Automated Cartography, in Communication of the ACM June 1981 Volume 24 Number 6 and in many other publications.

Figure 4:
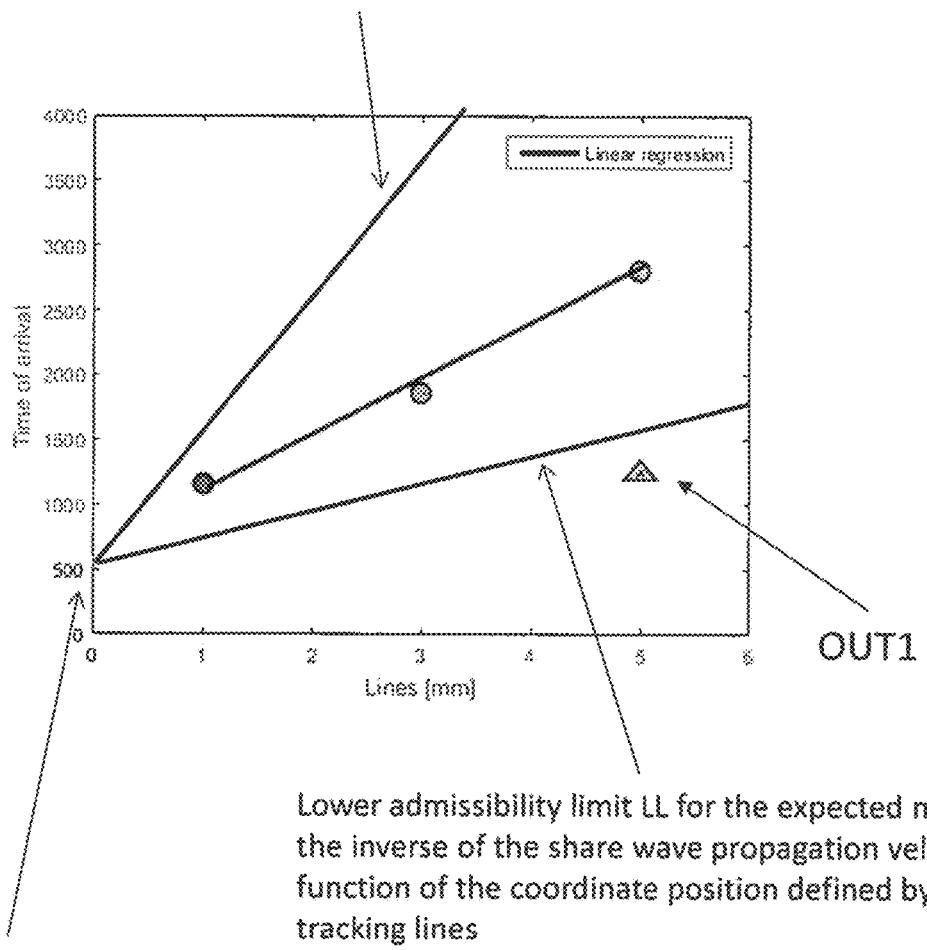
FIG. 4 show a graph representing the regression line calculated on the values of the time of arrivals as a function of the lateral position i.e. of the tracking line position at which the time of arrival has been determined and in which graph the limits for the maximum admissible velocity of the shear wave and the minimum admissible velocity of the shear wave according to the expected values for these velocities are drawn as a function of the lateral position of the tracking lines.

FIG. 4 shows a further embodiment according to which outliers can be also filtered out, i.e. excluded from the data on which the RANSAC or a simple regression algorithm is applied for determining the best fitting regression line. The further steps comprise determining limits of the values for the maximum velocity and the minimum velocity of the shear wave which are expected at the positions of the tracking lines and according to a specific application of the shear wave elasticity imaging mode. Two limit lines UL and LL can be determined as shown in FIG. 4. The candidate times of arrivals as a function of the lateral position which falls outside the field defined by the upper and the lower limit UL, LL are automatically excluded from the database on which the linear regression according to the method of the present invention or according to any traditional method is carried out. In FIG. 4 the outlier OUT1 is below the lower limit line LL ad thus is not been considered for determining the regression line best fitting the data. The two limits UL and LL shall depart from the starting time of the shear wave propagation at the excitation point. as indicated by the point SW.

Figure 5A:
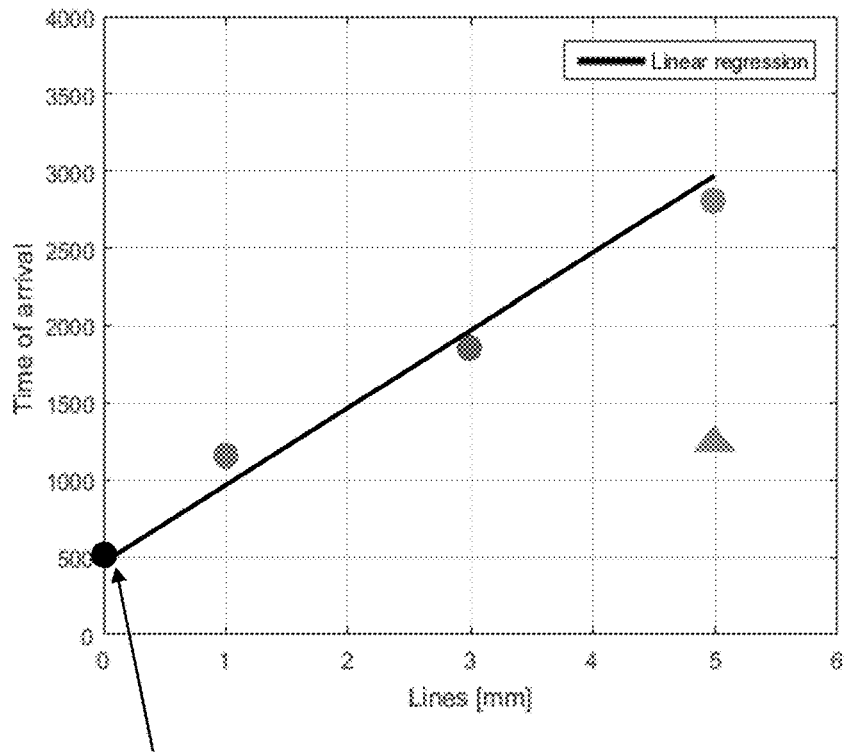
FIG. 5A is a representation of the diagram of the regression line calculated on the values of the time of arrivals as a function of the lateral position of the tracking lines in which data also the point representing the time of start of the shear wave at the excitation point of the shear wave is considered for determining the regression.

As illustrated in FIG. 5A, this starting point can be added to the data for calculating the regression line either applying a traditional regression method or the one according applying the RANSAC algorithm and described above and the said two variants may also be combined with the embodiment according to FIG. 4. Since the time of start point SW can be determined considering theoretical relations, this point is not affected by noise or errors introduced by the measuring process and has a higher reliability than the measured data. According to a variant embodiment in calculating the regression line using one or more of the previously described variants weights can be applied to the data which give more strength to the starting point SW in relation to the other data.

Figure 5B:
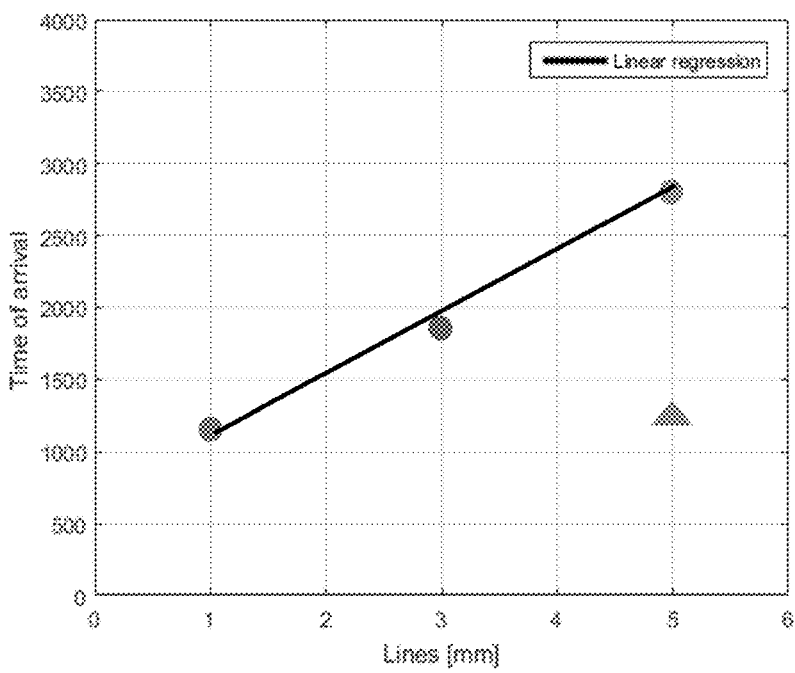
FIG. 5B is a comparison result illustrated in an analogous diagram as in FIG. 5A in which the regression line has been calculated without considering the point representing the time of start of the shear wave in the data to which linear regression is applied.

FIG. 5B shows the same result of the calculation of the regression line in which the starting point SW has not been considered. The influence of the outlier on the slope is stronger in the regression line of FIG. 5B than in the one of FIG. 5A so that a higher precision in determining the velocity is obtained when considering also the point SW.

Figure 10A:
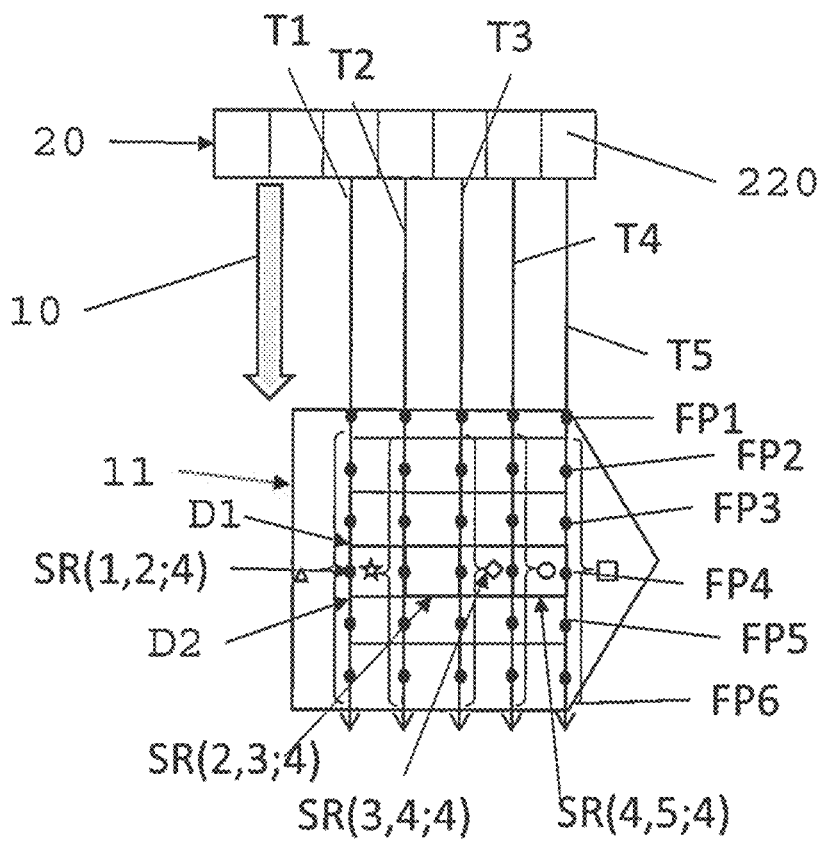
FIG. 10A is a schematic more detailed representation of FIG. 2 in which the shear wave depth range is shown and the tracking focal points along a certain number of tracking lines are represented and representing in a simplified way the principle of a two-dimensional share wave elasticity imaging mode.
Figure 10B:
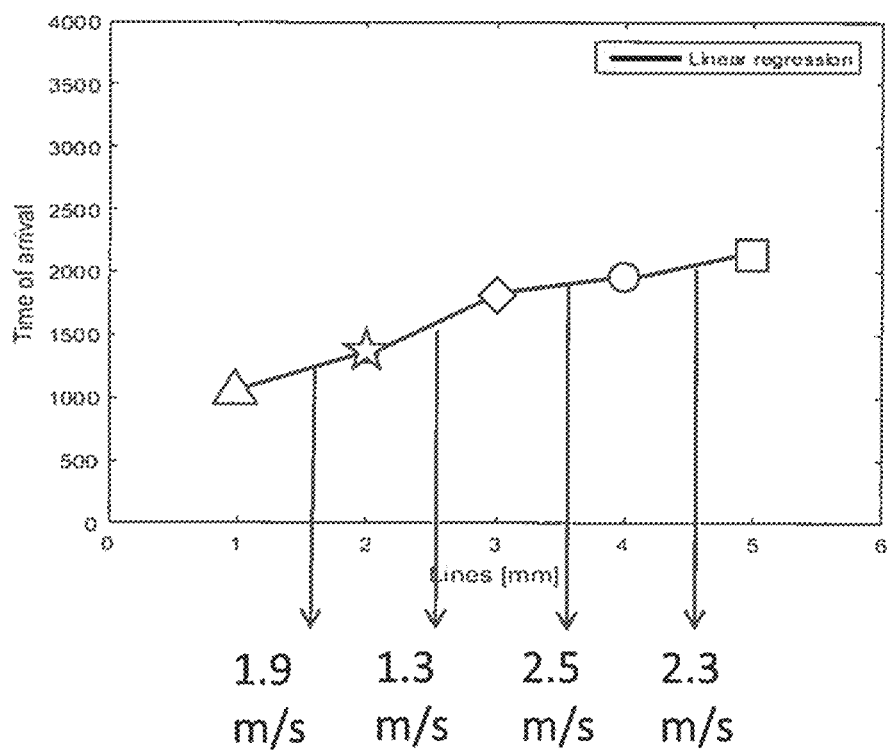
FIGS. 10B and 10C show an example of the method according to embodiments disclosed herein for calculating the shear wave velocity at a certain depth according to two different embodiments.
Figure 10C:
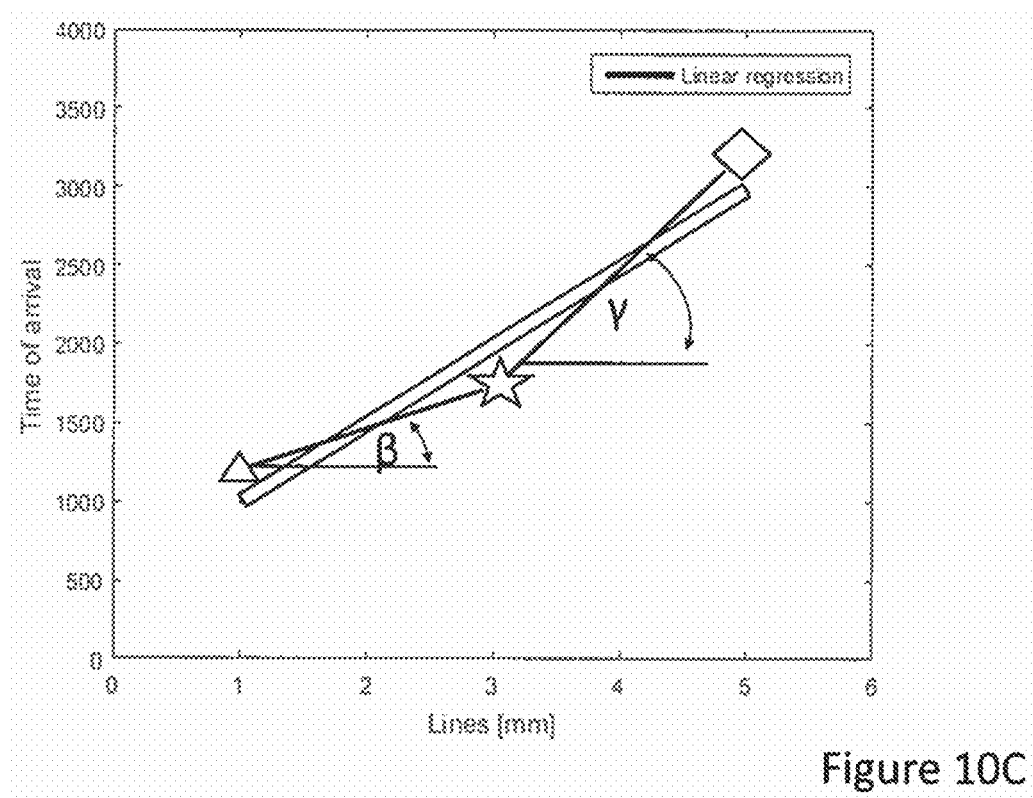

FIGS. 10A to 10C graphically illustrate the principle of a two-dimensional shear wave elasticity imaging mode. This mode can be combined with the above disclosed embodiments of the method for determining more accurate and reliable velocity data of the share wave propagation in considering the influence of the outliers in the measured data.

Here, in FIG. 10A, the probe 20 is represented diagrammatically as a linear array of transducers 220. The arrow 10 represents the tracking pulse focused at an excitation point or region along a certain line adjacent to the region of interest. The shear wave 11 is represented by the arrow and has a certain width in the depth direction i.e. in the direction of propagation of the tracking beams focused on tracking lines T1, T2, T3, T4 and T5 and the direction of propagation of the shear wave is indicated by the arrow like shape. The tracking beams T1 to T5 are focused each one along a line of sight of a plurality of lines of sight which are distributed over the extension of the region of interest. The term lateral means here in the direction of propagation of the shear wave 11.

Along each tracking line the corresponding tracking beam is focused at a certain number of tracking focal points FP1 to FP6 or segments of the tracking line corresponding each one to a range of depth in the propagation direction of the tracking line. The depth ranges or the tracking points are positioned at different depth in the region of interest.

Ultrasound tracking beams are repeatedly transmitted focused along the tracking lines and the received data are processed for determining the displacements of the tissue in the region of interest caused by the propagation of the shear wave.

The displacement is a mean displacement since it is averaged in the space, by grouping the displacement measurement between near pixels. On each tracking line, and at each tracking point along the corresponding tracking line the measurement of the displacement is repeated over time to form a sample curve representing the passage of the shear wave.

According to an embodiment such curve may be filtered by a moving mean such to eliminate noise.

For each tracking line and at each tracking focal point at the different depth the measured curve shows the displacement at the corresponding focal point as a function of time.

According to the present embodiment, the peak or the local maxima of the measured displacement is defined to find the shear wave propagation speed: the peak instant on each line of sight and at each tracking focal point FP1 to FP6 related to the known distance of the lines of sight from each other allows the propagation speed to be calculated.

Identifying the peak or the local maxima is the most simple and advantageous operation, but as an alternative it is possible to consider other significant points of the curve such as for example the maximum slope point or the correlation between the curves or the difference between curves.

According to the above process, the displacements inside the region of interest along each of the tracking lines and at the different depth of the tracking focal points are considered, to reconstruct the shear wave propagation pattern by the measurement of all the tracking lines and the shear wave speed obtained from the said propagation pattern may be processed for calculating the distribution of the elasticity parameter along the region of interest.

According to an embodiment the examination may be structured in repeated acquisition sequences, and each sequence comprises the transmission of an acoustic excitation pulse at the excitation point and a measurement of the displacements at the tracking focal points of a single tracking line or of a plurality of tracking lines acquired in parallel.

When the measurement of the displacements induced by the propagation of the shear wave occurs line by line it is necessary to transmit an excitation pulse for each of the measurements on the different lines of sight acquired individually or in parallel.

For example, it is possible to acquire one line of sight at a time or two or four lines of sight at a time in parallel, with standard B-mode imaging techniques.

Tracking of the displacement data along two or more of the tracking lines can also be carried out in an interleaved manner for the two or more tracking lines relatively to each shear wave generation event after a shear wave excitation pulse of a sequence of excitation pulses.

According to an embodiment, such sequence of excitation pulses has a limited number of excitation pulses transmitted with a certain repetition frequency and each series of excitation pulses is interrupted for a certain period by a cooling period before being carried out again. The B-mode image acquisition and the corresponding image may be frozen for the time during which a series of excitation pulses is being transmitted and the B-mode image may be refreshed by a new image acquisition during the cooling period between the repetition sequences of excitation pulses.

Such feature has also the advantage of allowing hardware to be prepared to perform a new transmission series of excitation pulses, and at the same time of allowing the probe and the tissues to cool.

In a further embodiment for each tracking line, before the transmission of the shear wave excitation pulse, one or more reference measurements on the line of sight under examination are carried out. Thus, the displacement at each of the tracking points can be measured in relation to a reference condition where the tissue in the region of interest is not disturbed by the passage of the shear wave.

According to a further embodiment, the data detected by the measurement of the shear wave are processed for filtering possible artifacts. Preferably such processing is carried out before the calculation of the displacement on each line of sight and the following calculation of the shear wave propagation speed.

In one embodiment, an ECG signal is recorded and the generation of ultrasound beams and the measurement of the displacement of pixels in the image induced by the shear wave passing through the region of interest are synchronized with the ECG signal.

Thus, the method can perform a triggering on the heartbeat, in order to try to suppress as much as possible the movement-related artefacts, for which the shear wave imaging is very sensitive.

This embodiment can be used for the measurement of the elasticity of any biological tissue involved by the cardiac movement, and it is particularly advantageous in relation to the measurement on the left part of the liver, that is the liver part affected by the heartbeat.

The processing of the acquired data substantially is divided in the following 4 macro-steps:

I. Processing the repetitions of the acquisition of a line of sight to obtain the extraction of the pattern over time of the displacements of the tissue on such line of sight at each tracking focal point within the region of interest 2;

II. Processing the set of results deriving from the previous steps in order to obtain the shear wave speed distribution in the region of interest and out of these data the one or more elasticity parameters in different sub regions of the region of interest III. Generating a graphic representation of the calculated values of the elasticity parameter distribution in the region of interest in the form of an elasticity image by applying to the image pixels representing the corresponding sub region of the region of interest appearance features as a function of the said elasticity parameters.

IV. Combining this elasticity image to the anatomical image of the region of interest, i.e. the B-mode image of the region of interest by maintaining the same scaling and the same topological relation of the sub regions in the elasticity image with the anatomical structure in the region of interest.

FIG. 10B shows the result of the linear regression method according to one or more of the previous embodiments of FIGS. 3A to 5A applied to the time of arrival of the shear wave determined at tracking focal points $T(m,n)$ with m indicating the index of the tracking lines 1 to 5 and n indicating the index of the tracking point at different depth n=1, 2, 3, 4, 5, 6 at the same depth and along a tracking line m. The displacement curves as a function of times at each tracking point of the same depth along the different tracking lines allows for determining a speed value for the shear wave in the said sub-region and calculating corresponding elasticity parameters. This can be done for each sub region $SR(m,m+1;n)$ of the region of interest which sub region is delimited laterally by two adjacent tracking lines $T(m)$, $T(m+1)$ and in the direction of depth by two adjacent lines delimiting a depth range along each tracking line as indicated by D1 and D2 in FIG. 1B. The said depth range is a region centred in depth along each tracking line at a tracking focal point $TP(n)$ on the same tracking line $T(m)$, $T(m)$, $T(m+1)$, $T(m+2)$, ..., $T(m+z)$, where z is a natural number and having a certain length along the tracking line.

According to the above, in relation to the term tracking focal point, in the present description and in the claims, the meaning of this term shall include the term tracking depth range along a tracking line.

Indeed, after each tracking pulse the reflected data along one or more lines of sight is determined. For each line of sight, the RF signal or the data expressed in phase and quadrature deriving from the reflected acoustic tracking beams after the beamforming in reception is distributed over a series of adjacent segments having predefined length along the corresponding line of sight. The segments are representative of a certain depth range along the tracking line. Each segment is considered as representative of a certain depth.

According to an embodiment the depth for which the segment is considered representative coincides with the central point of the segment or with the central sample of the data or signal relating to a corresponding depth range.

According to an embodiment these segments are cross correlated with analogous segments at the same depth range relating to another tracking pulse which has been emitted before the excitation of the shear wave and having the function of a reference. This operation cross correlating the tracking data in the region of interest before the excitation of the shear wave and after the excitation of the shear wave allows for determining the displacement caused by the propagation in the region of interest of the shear wave.

Generalising, since other techniques are possible for determining the displacements caused by the shear wave passage in the region of interest out of the reference data and the data after the shear wave excitation, according to a common technique in elastography, the displacement is measured by comparing the reference data acquired in the region of interest before the shear wave excitation and the data acquired after the shear wave excitation and during its propagation in the region of interest.

According to an alternative embodiment, the displacement caused by the shear waves may be calculated also using a differential technique by cross-correlating the signal obtained from the reflection of a current tracking pulse along a line of sight with the signal obtained from the reflected tracking pulse focused on the same line and emitted at a time immediately preceding the said current tracking pulse and repeating this for a sequence of tracking pulses transmitted on the same tracking line, thereby obtaining a measure of the variation of the displacement induced by the shear wave at the same local position at different following time instants, i.e. as a function of time. The displacement curve may be determined by integrating these data over time.

According to one embodiment of the present method and system there is provided the said step of measuring the displacements induced by the shear wave in a region of interest by comparing and more specifically cross correlating the tracking data obtained along the one or more tracking lines in an acquisition step before the excitation of the shear wave (reference data) and the tracking data obtained by the acquisitions along the tracking lines after the shear wave excitation.

According to an embodiment adjacent segments may overlap each other for a certain length.

Making use of reference measurements in relation to the above definition of the depth range, the minimum dimension of a pixel or of an image unitary area of the elasticity map along the depth direction is determined as the pitch between a depth segment and the following one considering also an overlap if it is present. The sub-region SR I thus limited laterally by two adjacent tracking lines and centred on a tracking point TP(n).

In FIG. 10A the speed of the shear wave in the sub regions SR(1,2;4), SR(2,3;4), SR(3,4;4), SR(4,5;4) is calculated as the linear regression between the displacement peaks determined at the tracking point 4 and on each pair of adjacent tracking lines 1,2; 2,3; 3,4; 4,5. Examples of speed values determined from the different gradients of the lime passing through the displacement data.

As indicated in FIG. 3A for only the first three tracking lines, at each tracking point the curve represents the displacement as the function of time. The time of arrival at a certain tracking line is set as the time at which the displacement peak has been measured and the velocity is determined as the inverse of the gradient of the linear regression of the time of arrival as a function of the tracking line position.

As indicated by the symbols the three curves represent the displacement as a function of time at the first three tracking lines.

FIGS. 3B and 3C represent the diagrams where the time of arrival is indicated as a function of the three tracking lines T1, T2 and T3 of which the time dependent displacement curves are shown in FIG. 3A. In the case of FIG. 3B the resolution of the distribution of elasticity parameters is calculated over three adjacent tracking lines, so that three subregion for which the velocity of the shear wave is estimated is the one encompassed by three adjacent tracking lines. Differently FIG. 10B represents an embodiment of the process in which the highest resolution is obtained for the velocity data since the value of the velocity of the shear wave is calculated for each sub-region encompassed by only two adjacent tracking lines which is the smallest possible sub regions determined by the lateral pitch (distance) between adjacent tracking lines and the depth pitch between adjacent tracking points.

Considering FIG. 10C, the result of the linear regression between the time of arrival respectively on the pair of tracking lines T1 and T2 and T2 and T3 at a certain depth shows that the lines passing through the points have two different inclinations or gradients.

FIG. 10C shows the situation of FIG. 10B limited to the first three tracking lines. Referring also to FIG. 10A, the sub regions in which the velocity data is calculated are delimited by three tracking lines which in this case are the three lines T1, T2 and T3. In relation to the dimensions of the sub region in direction of depth the same dimension as in the previous example are considered without any limitation to the fact that the sub regions can have different dimensions in each of the two directions which are independent one from the other. The linear regression is carried out using the determined time of arrivals of the shear wave at each of the three lines and the inclination of the line, i.e. the angle $\alpha$ is different from the angles $\beta$ and $\gamma$ in FIG. 10C.

According to an embodiment by defining the smallest sub-region of the region of interest as the one delimited by two adjacent tracking lines, i.e. lines of sight, there is the possibility to set the resolution of the calculated velocity data and thus of the calculated elasticity parameters within the region of interest at different levels. When the sub-region dimension is set as the one delimited by two adjacent trackling lines, then the maximum resolution is obtained since the velocity data of the said sub-region is determined by the inverse of the time of arrival of the shear waves at the said two tracking lines according to the solutions illustrated at FIGS. 10B and 10C. Reducing the resolution but enhancing the statistical reliability can be achieved by defining as a subregion the one delimited by every third tracking line. This means a sub region delimited by two non directly adjacent tracking lines and encompassing at least one intermediate tracking line. The sub region in the image could be relative to a triplet of tracking lines such as the one according to FIG. 3B or 3C and the entire region of interest could be covered by shifting the line triplet by at least one line for each sub-region. So for example the lines used for the calculation of the value in the following sub region will be the lines T2, T3, and T4 and the elasticity parameter of the next sub region will be calculated by using the measurements along the lines T3, T4 and T5 which will also be the last sub region possible since only 5 tracking lines are considered in the present simplified example.

This way of proceeding may be applied considering the tracking points at different depth, so in the depth direction each sub region may have a dimension corresponding to the region between two adjacent tracking points n, n+1 or between three tracking points or four or five tracking points, similarly to the dimensions of the sub regions in the lateral direction which can be four sub regions having a lateral dimension corresponding to the distance between two adjacent tracking lines or three sub regions having a lateral dimension corresponding to the distance of two tracking lines or two sub regions corresponding to the distance of four tracking lines or only one region corresponding to the lateral dimension of the entire region of interest.

Figure 11A:
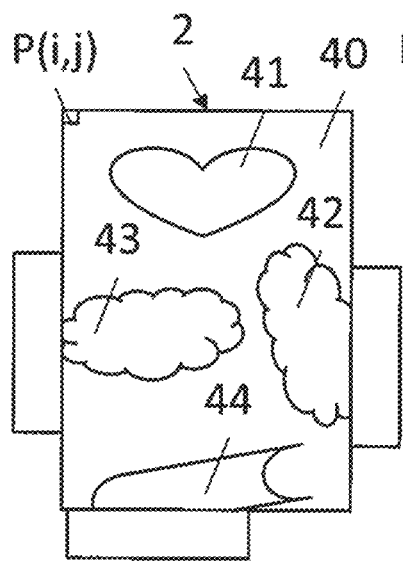
FIGS. 11A to 11E show the image representing the elasticity parameters according to different choices of application of the two-dimensional share wave elasticity imaging mode for determining the shear wave velocity and therefrom the elasticity parameters.
Figure 11B:
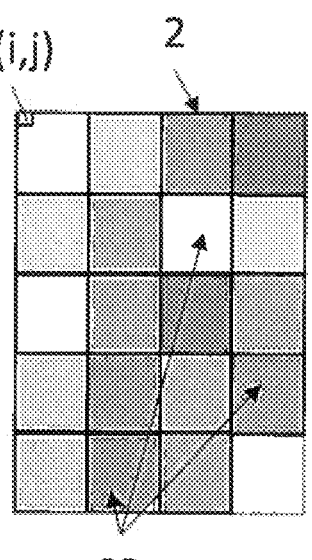

FIG. 11a shows a diagrammatic example of a region of interest in which different tissues indicated by 40, 41, 42 43 and 44 are present. FIG. 11B shows an example of a graphic representation of the shear wave elastography imaging in which the values of the shear wave velocity or of the elasticity parameter determined for each sub region SR as defined according to the previous disclosure are represented by a different appearance of the corresponding pixels P(i,j) in the said sub region. In FIG. 11B only one pixel as a sample is shown for clarity sake. The pixel P(i,j) in the elasticity image of FIG. 11B corresponds to the pixel P(i,j) in the B-mode image of the region of interest in FIG. 11A. Normally the B-mode image is represented by modulating the appearance of the image pixels according to a grey scale. The different values of the velocity of the shear wave and/or the corresponding elasticity parameter can be represented by means of a monochromatic scale using a colour different than the grey or by a polychromatic scale. In the present example since colours are not admitted the different values of the velocity of the shear wave or of the corresponding elasticity parameter are represented in a grey scale.

As it appears, the pixels p(i,j) of the B-mode image in the region of interest are modified in relation to their appearance according to a monochromatic different from the grey scale or a polychromatic scale in the image representing the velocity or elasticity data in the different sub regions of the region of interest, maintaining nevertheless the same topological relation to the pixels of the B-mode image.

Figure 11C:
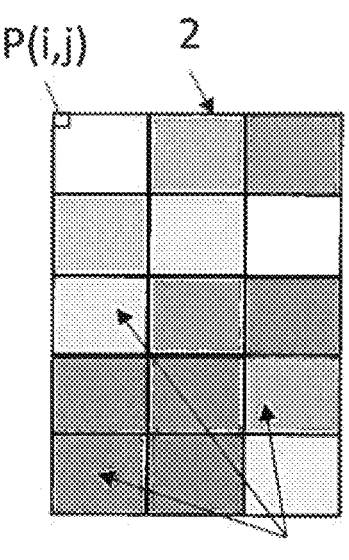

FIG. 11C shows the elasticity image obtained according to the embodiment of FIG. 11C in which the velocity data is determined by using three lines at the time. Both images 11B and 11C maintains the same dimensions of the sub regions which is corresponding to the distance of two adjacent tracking points along the tracking lines as indicated in FIG. 10A.

Figure 11D:
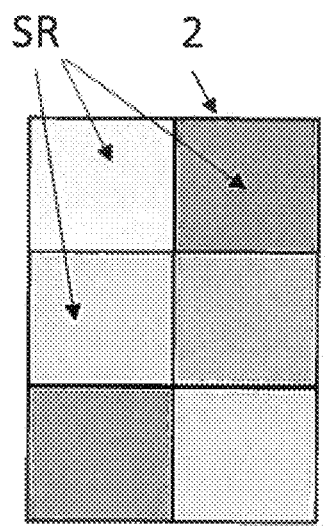

FIG. 11D shows an example of the elasticity image obtained by the present method in which four tracking lines are used for determining the velocity of the shear wave and the corresponding elasticity parameter, while in the direction of depth four tracking points are used and the time dependent curves are obtained by combining the displacement data of four following tracking points of the six available according to FIG. 10B on each tracking line.

Figure 11E:
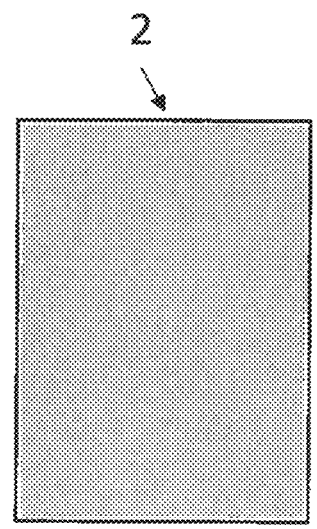

FIG. 11E corresponds to the traditional so-called one-dimensional shear wave elastography method in which the displacement curves along each tracking line are determined by combining the measured displacements at every tracking point and the velocity of the shear wave is determined by carrying out the regression in using the maxima of the displacement curves of all the tracking lines.

According to a further embodiment which can be provided alternatively or in combination with the above, the elastic image according to one of more of the examples of FIGS. 11B to 11E can be displayed combined with the B-mode image at least of the region of interest.

According to a first embodiment the elasticity image can be combined to the B-mode image by displaying the elasticity image overlapped to the B-mode image and with a certain degree of transparency. This can be obtained by weighting the parameters determining the appearance of the corresponding pixel in the image reproducing the shear wave velocity or the elasticity parameter and adding the said weighted parameters to the parameters determining the pixel appearance according to the grey scale in the B-mode image.

According to an embodiment, the pixel appearance parameter is determined according to a HSL or HIS or HSV colour space and the pixel appearance as a function of the corresponding elasticity parameter is determined by the Hue parameter defining a certain colour and by the saturation parameter of the colour in relation to the grey scale image.

According to still a further embodiment, the elasticity image can use the parameters for determining the pixel appearance in the HSV or HSL or HIS colour space for representing the velocity or the elastic parameter values related to each pixel of the region of interest and also the statistical reliability of the said values, such as the corresponding standard deviation or other parameters representing the statistical fitness of the estimation algorithm.

In this case the image can still be superimposed to the b-mode image of the region of interest or for simplifying the interpretation this kind of image can be reproduced beside the B-mode image of the region of interest alone or combined with the image representing the distribution of the velocity or of the elastic parameters according to the previous embodiment in which only the values of these parameters are graphically represented.

Figure 6:
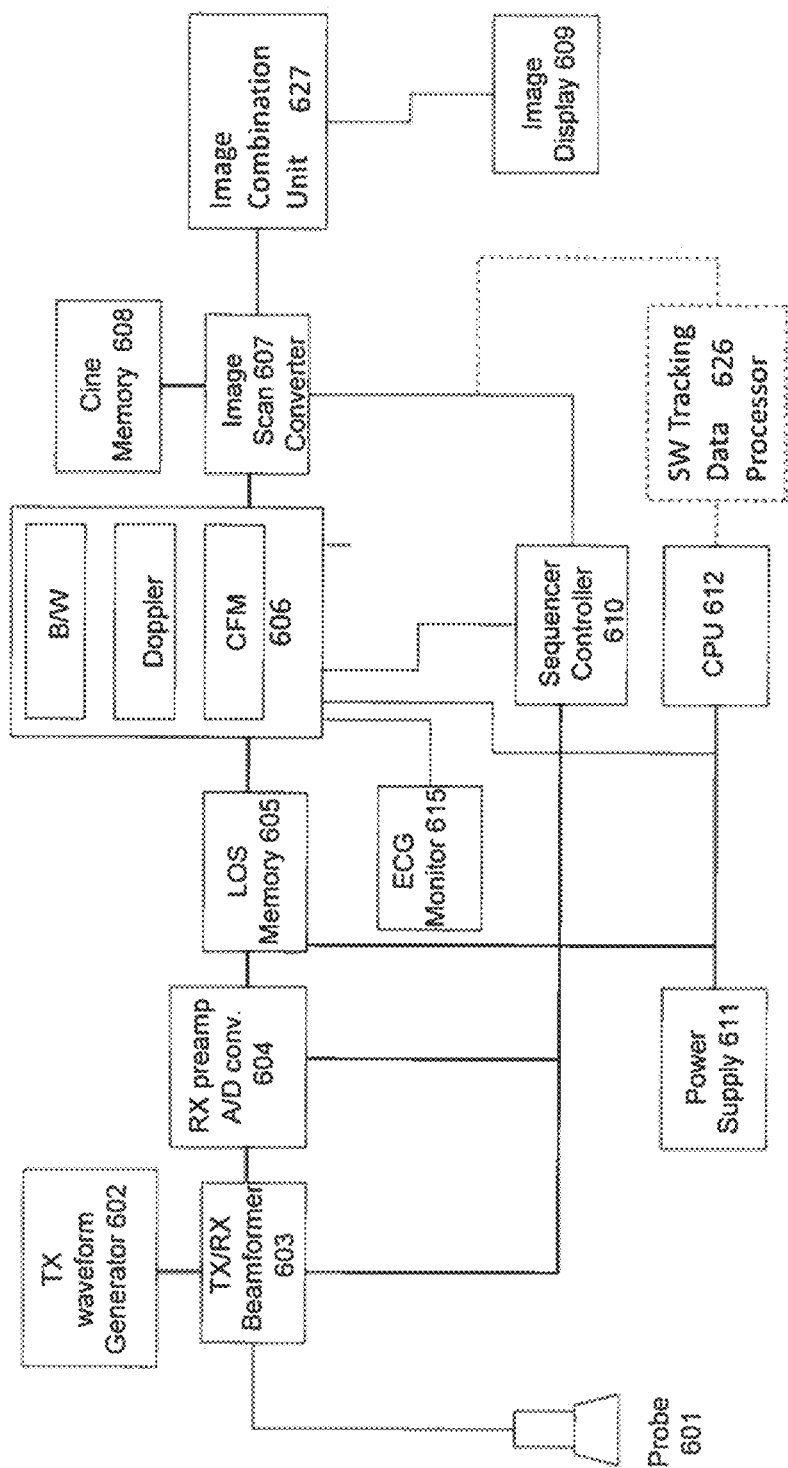
FIG. 6 show a high-level block diagram of an ultrasound system for carrying out shear wave elasticity imaging.

FIG. 6 illustrates a high-level block diagram of an ultrasound system. Portions of the system (as defined by various functional blocks) may be implemented with dedicated hardware, such as transmit/receive (TX/RX) driving/preamp and power switching circuitry, which may utilize analog components. Digital components, DSPs and/or FPGAs, may be utilized to implement the sequencer controller and the timing generator.

The ultrasound system of FIG. 6 includes one or more ultrasound probes 601, 620. The probe 601 may include various transducer array configurations, such as a one-dimensional array, a two-dimensional array, a linear array, a convex array and the like. The transducers of the array may be managed to operate as a 1D array, 1.25D array, 1.5D array, 1.75D array, 2D array, 3D array, 4D array, etc.

The ultrasound probe 601 is coupled over a wired or wireless link to a beamformer 603. The beamformer 603 includes a transmit (TX) beamformer and a receive (RX) beamformer that are jointly represented by TX/RX beamformer 603. The beamformer 603 supplies transmit signals to the probe 601 and performs beamforming of "echo" signals that are received by the probe 601.

A TX waveform generator 602 is coupled to the beamformer 603 and generates the transmit signals that are supplied from the beamformer 603 to the probe 601. The transmit signals may represent various types of ultrasound TX signals such as used in connection with B-mode imaging, color Doppler imaging, pulse-inversion transmit techniques, contrast-based imaging, M-mode imaging and the like. In accordance with embodiments herein, the transmit signals include acoustic disturbance ultrasound (ACU) beam (10, in FIG. 2) that are directed at select excitation points or regions (1 in FIG. 2). The ACU beams are configured to generate shear waves as described herein.

The beamformer 603 performs beamforming upon received echo signals to form beamformed echo signals in connection pixel locations distributed across the region of interest. For example, in accordance with certain embodiments, the transducer elements generate raw analog receive signals that are supplied to the beamformer. The beamformer adjusts the delays to focus the receive signal along a select receive beam and at a select depth within the ROI. The beamformer adjusts the weighting of the receive signals to obtain a desired apodization and profile. The beamformer sums the delayed, weighted receive signals to form RF beamformed signals. The RF beamformed signals are digitized at a select sampling rate by the RX preamp and A/D converter 604. The RF beamformed signals are converted to I,Q data pairs.

The TX waveform generator 902, TX/RX beamformer 603 and A/D converter 604 cooperate to generate the acoustic disturbance ultrasound beams (10) directed at the excitation point (1). The acoustic disturbance ultrasound beams are configured to produce shear waves (11) that have directions of propagation extending laterally from the directions of propagation of the acoustic disturbance ultrasound beams (10). The RF data or the I, Q data pairs are saved as image pixels in the line of sight (LOS) memory. For example, the LOS memory may include LOS memory portions associated with each line of sight through the ROI. The I,Q data pairs, defining the image pixels for corresponding individual ROI locations along a corresponding LOS, are saved in the correspond LOS memory portion. A collection of image pixels (e.g., I,Q data pairs) are collected over time and saved in the LOS memory 605. The image pixels correspond to tissue and other anatomy within the ROI. As the ROI experiences the shear waves, the tissue and other anatomy in the ROI moves in response to the shear waves. The collection of image pixels captures the movement of tissue other anatomy within the ROI.

In embodiments, a dedicated sequencer/timing controller 610 may be programmed to manage acquisition timing which can be generalized as a sequence of firings aimed to locally generate shear waves aside the measurement box followed by tracking firings to monitor transition of the shear waves through the acquisition lines (LOS) in the measurement box (corresponding to the ROI). Optionally, idle phases can be added to control heating of the probe and manage compliance with safety emission regulations.

A sequence controller 610 manages operation of the TX/RX beamformer 603 and the A/D converter 604 in connection with transmitting ADU beams and measuring image pixels at individual LOS locations along the lines of sight. The sequence controller 610 manages collection of reference measurements and shear-wave induced measurements. The sequence controller 610 provides a pause period between a last measurement along one tracking line coincident with one line of sight and a first measurement along a following tracking line coincident with a following line of sight.

One or more processors 606 perform various processing operations as described herein. The CPU 612 may perform one or more of the operations described herein in connection with generation of shear waves, measurement of displacement, calculation of displacement speed, calculation of stiffness values and the like.

Among other things, the processor 606 and/or CPU 612 analyse the image pixels to measure displacement of the image pixels or controls an optional dedicated shear wave tracking data processor 626. The processor 606 and/or the CPU 612 and or the optional shear wave data processor measure the displacement at image pixels for the plurality of lines of sight placed in the region of interest. The lines of sight are located at different predetermined laterally staggered distances from the excitation point (1), (4).

The processor 606 and/or CPU 612 or optionally a dedicated shear wave tracking data processor 626 also calculates a stiffness value based on the speed of the shear wave according to one or more of the examples describe above.

As explained herein, the processor 606 and/or CPU 612 or the dedicated processor 626 obtaining one or more reference measurements for a plurality of lines of sight in the region of interest, prior to generating the first and second shear waves. According to an embodiment, the processor 606 and/or CPU 612 or the optional dedicated processor 626 measure the shear waves (11 include measuring mean displacement over time of the tissue along a plurality of line of sights and identifying a peak of the mean displacements.

For example, the measurements by the processor 606 and/or CPU 612 or the optional dedicated processor 626 may include calculating a cross-correlation between the measurements associated with the shear waves and a reference measurement obtained independent of the shear waves. The processor 606 and/or CPU 612 or the optional dedicated processor 626 measure displacement over time of the tissue along a plurality of line of sights and calculates speeds of the shear waves (11) based, in part, on distances of the corresponding lines of sight from the excitation point (1).

The processor 606 and/or CPU 612 also performs conventional ultrasound operations. For example, the processor 606 executes a B/W module to generate B-mode images. The processor 606 and/or CPU 612 executes a Doppler module to generate Doppler images. The processor executes a Color flow module (CFM) to generate color flow images. The processor 606 and/or CPU 612 may implement additional ultrasound imaging and measurement operations. Optionally, the processor 606 and/or CPU 612 may filter the displacements to eliminate movement-related artefacts.

Processor 606 and/or CPU 612 are configured by executing a program coding the corresponding instructions to carry out the steps describe according to one or more of the embodiments describe above and to carry out the RANSAC algorithm for determining the best fitting regression line according to the setting of the criteria of best fitting.

An image scan converter 607 performs scan conversion on the image pixels to convert the format of the image pixels from the coordinate system of the ultrasound acquisition signal path (e.g., the beamformer, etc.) and the coordinate system of the display. For example, the scan converter 607 may convert the image pixels from polar coordinates to Cartesian coordinates for image frames.

A cine memory 608 stores a collection of image frames over time. The image frames may be stored formatted in polar coordinates, Cartesian coordinates or another coordinate system.

An image display 609 displays various ultrasound information, such as the image frames and information measured in accordance with embodiments herein. For example, the image display 609 displays the stiffness values, displacement measurements, displacement speeds, and other information calculated in accordance with embodiments herein. The stiffness values, displacement measurements, displacement speeds, and other information may be displayed as image information, as numeric values, graphical information and the like. The display 609 displays the ultrasound image with the region of interest shown. Optionally, the display 609 may display indicia indicating the excitation points (1), where the indicia are overlaid on the ultrasound image and/or presented along opposite sides of the ultrasound image.

Optionally, the system of FIG. 6 may include an ECG monitor 615 that couples an ECG sensor to the patient and records an ECG signal indicative of the patient's heart rate. The processor 606 and/or sequence controller 610 synchronize the generation of acoustic disturbance ultrasound beams (10) and the measurement of the first and second displacements of the image pixels induced by the first and second shear waves (11) with the ECG signal.

The blocks/modules illustrated in FIG. 6 can be implemented with dedicated hardware (DPSs, FPGAs, memories) and/or in software with one or more processors.

A control CPU module 612 is configured to perform various tasks such as implementing the user/interface and overall system configuration/control. In case of fully software implementation of the ultrasound signal path, the processing node usually hosts also the functions of the control CPU.

A power supply circuit 611 is provided to supply power to the various circuits, modules, processors, memory components, and the like. The power front-end may be an A.C. power source and/or a battery power source (e.g., in connection with portable operation).

Optionally, in point Shear Wave acquisition, the RX tracking lines (line of sights—LOSs) may be temporarily stored, either as pure RF or as I/Q data, in the front-end local memories. The processing may be implemented by a dedicated processor module 606 and/or a CPU 612. Processed data, may be formatted as shear wave speed measurements or stiffness values. These, are then added to the ancillary data of the field-of-view under scan and properly reported as an overlay to the image displayed on system's monitor.

According to a further feature, an image combination unit 627 may be present in which the B-mode image data of at least of a region of interest and the corresponding graphic representation as an image of the velocity of the shear wave or of the elasticity parameter determined from said velocity data is combined for the superimposed display of the B-mode image and of the image representing the shear wave velocity and/or the elasticity features determined for the corresponding pixels in the B-mode image. The representation as an image of the velocity or of the corresponding elasticity parameter values and the combination of this image with the B-mode image can be carried out according to one of the previously disclosed methods.

Figure 7:
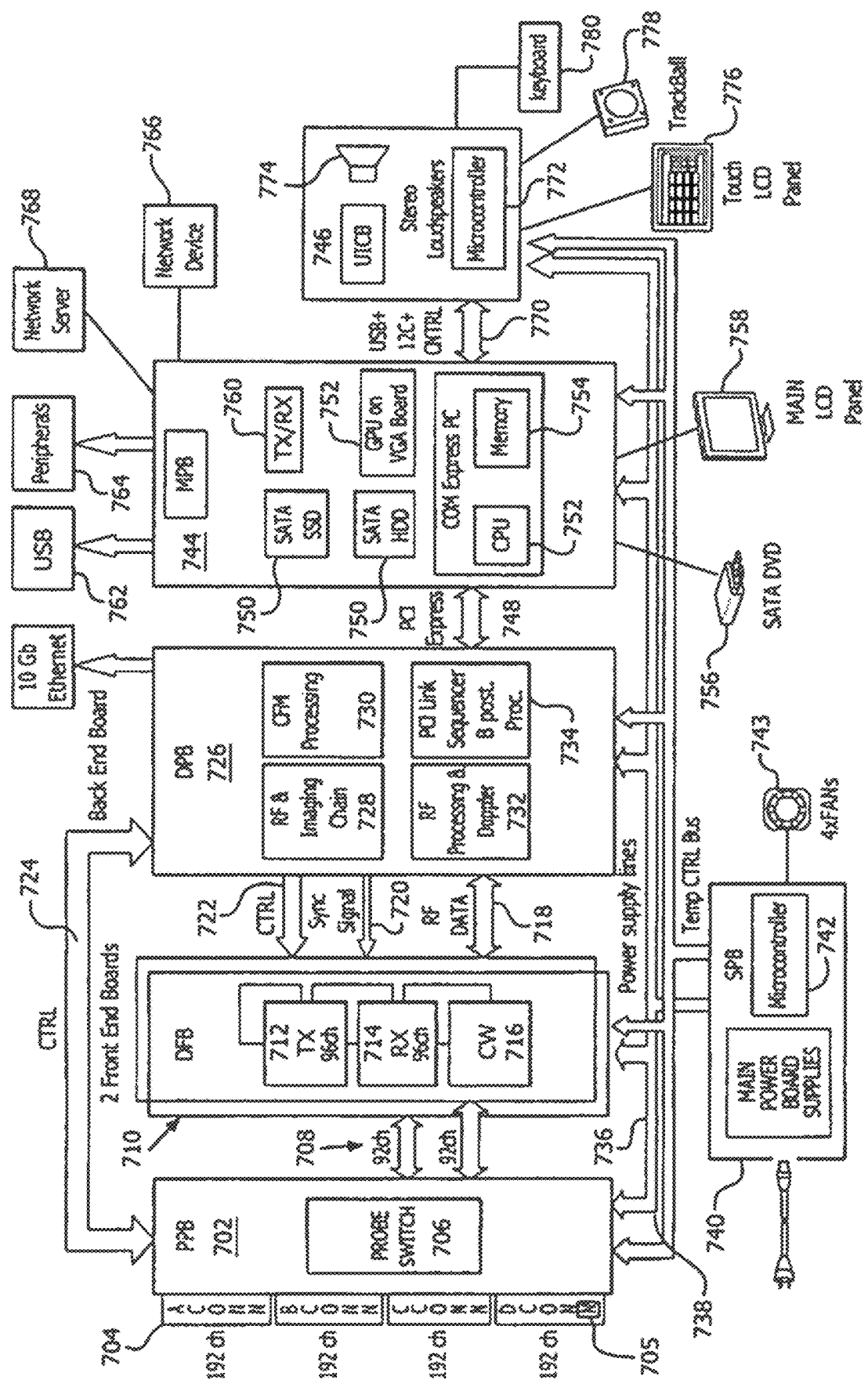
FIG. 7 illustrates a block diagram of an ultrasound system formed in accordance with an alternative embodiment.

FIG. 7 illustrates a block diagram of an ultrasound system formed in accordance with an alternative embodiment. The system of FIG. 7 implements the operations described herein in connection with various embodiments. By way of example, one or more circuits/processors within the system implement the operations of any processes illustrated in connection with the figures and/or described herein. The system includes a probe interconnect board 702 that includes one or more probe connection ports 704. The connection ports 704 may support various numbers of signal channels (e.g., 128, 192, 256, etc.). The connector ports 704 may be configured to be used with different types of probe arrays (e.g., phased array, linear array, curved array, 1D, 1.25D, 1.5D, 1.75D, 2D array, etc.). The probes may be configured for different types of applications, such as abdominal, cardiac, maternity, gynaecological, urological and cerebrovascular examination, breast examination and the like.

One or more of the connection ports 704 may support acquisition of 2D image data and/or one or more of the connection ports 704 may support 3D image data. By way of example only, the 3D image data may be acquired through physical movement (e.g., mechanically sweeping or physician movement) of the probe and/or by a probe that electrically or mechanically steers the transducer array.

The probe interconnect board (PIB) 702 includes a switching circuit 706 to select between the connection ports 704. The switching circuit 706 may be manually managed based on user inputs. For example, a user may designate a connection port 704 by selecting a button, switch or other input on the system. Optionally, the user may select a connection port 704 by entering a selection through a user interface on the system.

Optionally, the switching circuit 706 may automatically switch to one of the connection ports 704 in response to detecting a presence of a mating connection of a probe. For example, the switching circuit 706 may receive a "connect" signal indicating that a probe has been connected to a selected one of the connection ports 704. The connect signal may be generated by the probe when power is initially supplied to the probe when coupled to the connection port 704. Additionally, or alternatively, each connection port 704 may include a sensor 705 that detects when a mating connection on a cable of a probe has been interconnected with the corresponding connection port 704. The sensor 705 provides signal to the switching circuit 706, and in response thereto, the switching circuit 706 couples the corresponding connection port 704 to PIB outputs 708. Optionally, the sensor 705 may be constructed as a circuit with contacts provided at the connection ports 704. The circuit remains open when no mating connected is joined to the corresponding connection port 704. The circuit is closed when the mating connector of a probe is joined to the connection port 704.

A control line 724 conveys control signals between the probe interconnection board 702 and a digital processing board 724. A power supply line 736 provides power from a power supply 740 to the various components of the system, including but not limited to, the probe interconnection board (PIB) 702, digital front-end boards (DFB) 710, digital processing board (DPB) 726, the master processing board (M PB) 744, and a user interface control board (UI CB) 746. A temporary control bus 738 interconnects, and provides temporary control signals between, the power supply 740 and the boards 702, 710, 726, 744 and 746. The power supply 740 includes a cable to be coupled to an external AC power supply. Optionally, the power supply 740 may include one or more power storage devices (e.g. batteries) that provide power when the AC power supply is interrupted or disconnected. The power supply 740 includes a controller 742 that manages operation of the power supply 740 including operation of the storage devices.

Additionally, or alternatively, the power supply 740 may include alternative power sources, such as solar panels and the like. One or more fans 743 are coupled to the power supply 740 and are managed by the controller 742 to be turned on and off based on operating parameters (e.g. temperature) of the various circuit boards and electronic components within the overall system (e.g. to prevent overheating of the various electronics).

The digital front-end boards 710 providing analog interface to and from probes connected to the probe interconnection board 702. The DFB 710 also provides pulse or control and drive signals, manages analog gains, includes analog to digital converters in connection with each receive channel, provides transmit beamforming management and receive beamforming management and vector composition (associated with focusing during receive operations).

The digital front-end boards 710 include transmit driver circuits 712 that generate transmit signals that are passed over corresponding channels to the corresponding transducers in connection with ultrasound transmit firing operations. The transmit driver circuits 712 provide pulse or control for each drive signal and transmit beamforming management to steer firing operations to points of interest within the region of interest. By way of example, a separate transmit driver circuits 712 may be provided in connection with each individual channel, or a common transmit driver circuits 712 may be utilized to drive multiple channels. The transmit driver circuits 712 cooperate to focus transmit beams to one or more select points within the region of interest. The transmit driver circuits 712 may implement single line transmit, encoded firing sequences, multiline transmitter operations, generation of shear wave inducing ultrasound beams as well as other forms of ultrasound transmission techniques.

The digital front-end boards 710 include receive beamformer circuits 714 that received echo/receive signals and perform various analog and digital processing thereon, as well as phase shifting, time delaying and other operations in connection with beamforming. The beam former circuits 714 may implement various types of beamforming, such as single-line acquisition, multiline acquisition as well as other ultrasound beamforming techniques.

The digital front-end boards 716 include continuous wave Doppler processing circuits 716 configured to perform continuous wave Doppler processing upon received echo signals. Optionally, the continuous wave Doppler circuits 716 may also generate continuous wave Doppler transmit signals.

The digital front-end boards 710 are coupled to the digital processing board 726 through various buses and control lines, such as control lines 722, synchronization lines 720 and one or more data bus 718. The control lines 722 and synchronization lines 720 provide control information and data, as well as synchronization signals, to the transmit drive circuits 712, receive beamforming circuits 714 and continuous wave Doppler circuits 716. The data bus 718 conveys RF ultrasound data from the digital front-end boards 710 to the digital processing board 726. Optionally, the digital front-end boards 710 may convert the RF ultrasound data to I, Q data pairs which are then passed to the digital processing board 726.

The digital processing board 726 includes an RF and imaging module 728, a colour flow processing module 730, an RF processing and Doppler module 732 and a PCI link module 734. The digital processing board 726 performs RF filtering and processing, processing of black and white image information, processing in connection with colour flow, Doppler mode processing (e.g. in connection with polls wise and continuous wave Doppler). The digital processing board 726 also provides image filtering (e.g. speckle reduction) and scanner timing control. The digital processing board 726 may include other modules based upon the ultrasound image processing functionality afforded by the system.

The modules 728-734 comprise one or more processors, DSPs, and/or FPGAs, and memory storing program instructions to direct the processors, DSPs, and/or FPGAs to perform various ultrasound image processing operations. The RF and imaging module 728 performs various ultrasound related imaging, such as B mode related image processing of the RF data. The RF processing and Doppler module 732 convert incoming RF data to I, Q data pairs, and performs Doppler related processing on the I, Q data pairs. Optionally, the imaging module 728 may perform B mode related image processing upon I, Q data pairs. The CFM processing module 730 performs colour flow related image processing upon the ultrasound RF data and/or the I, Q data pairs. The PCI link 734 manages transfer of ultrasound data, control data and other information, over a PCI express bus 748, between the digital processing board 726 and the master processing board 744.

The master processing board 744 includes memory 750 (e.g. serial ATA solid-state devices, serial ATA hard disk drives, etc.), a VGA board 752 that includes one or more graphic processing unit (GPUs), one or more transceivers 760 one or more CPUs 752 and memory 754. The master processing board (also referred to as a PC board) provides user interface management, scan conversion and cine loop management. The master processing board 744 may be connected to one or more external devices, such as a DVD player 756, and one or more displays 758. The master processing board includes communications interfaces, such as one or more USB ports 762 and one or more ports 764 configured to be coupled to peripheral devices. The master processing board 744 is configured to maintain communication with various types of network devices 766 and various network servers 768, such as over wireless links through the transceiver 760 and/or through a network connection (e.g. via USB connector 762 and/or peripheral connector 764).

The network devices 766 may represent portable or desktop devices, such as smart phones, personal digital assistants, tablet devices, laptop computers, desktop computers, smart watches, ECG monitors, patient monitors, and the like. The master processing board 744 conveys ultrasound images, ultrasound data, patient data and other information and content to the network devices for presentation to the user. The master processing board 744 receives, from the network devices 766, inputs, requests, data entry and the like.

The network server 768 may represent part of a medical network, such as a hospital, a healthcare network, a third-party healthcare service provider, a medical equipment maintenance service, a medical equipment manufacturer, a government healthcare service and the like. The communications link to the network server 768 may be over the Internet, a private intranet, a local area network, a wide-area network, and the like.

The master processing board 744 is connected, via a communications link 770 with a user interface control board 746. The communications link 770 conveys data and information between the user interface and the master processing board 744. The user interface control board 746 includes one or more processors 772, one or more audio/video components 774 (e.g. speakers, a display, etc.). The user interface control board 746 is coupled to one or more user interface input/output devices, such as an LCD touch panel 776, a trackball 778, a keyboard 780 and the like. The processor 772 manages operation of the LCD touch panel 776, as well as collecting user inputs via the touch panel 776, trackball 778 and keyboard 780, where such user inputs are conveyed to the master processing board 744 in connection with implementing embodiments herein.

Figure 8:
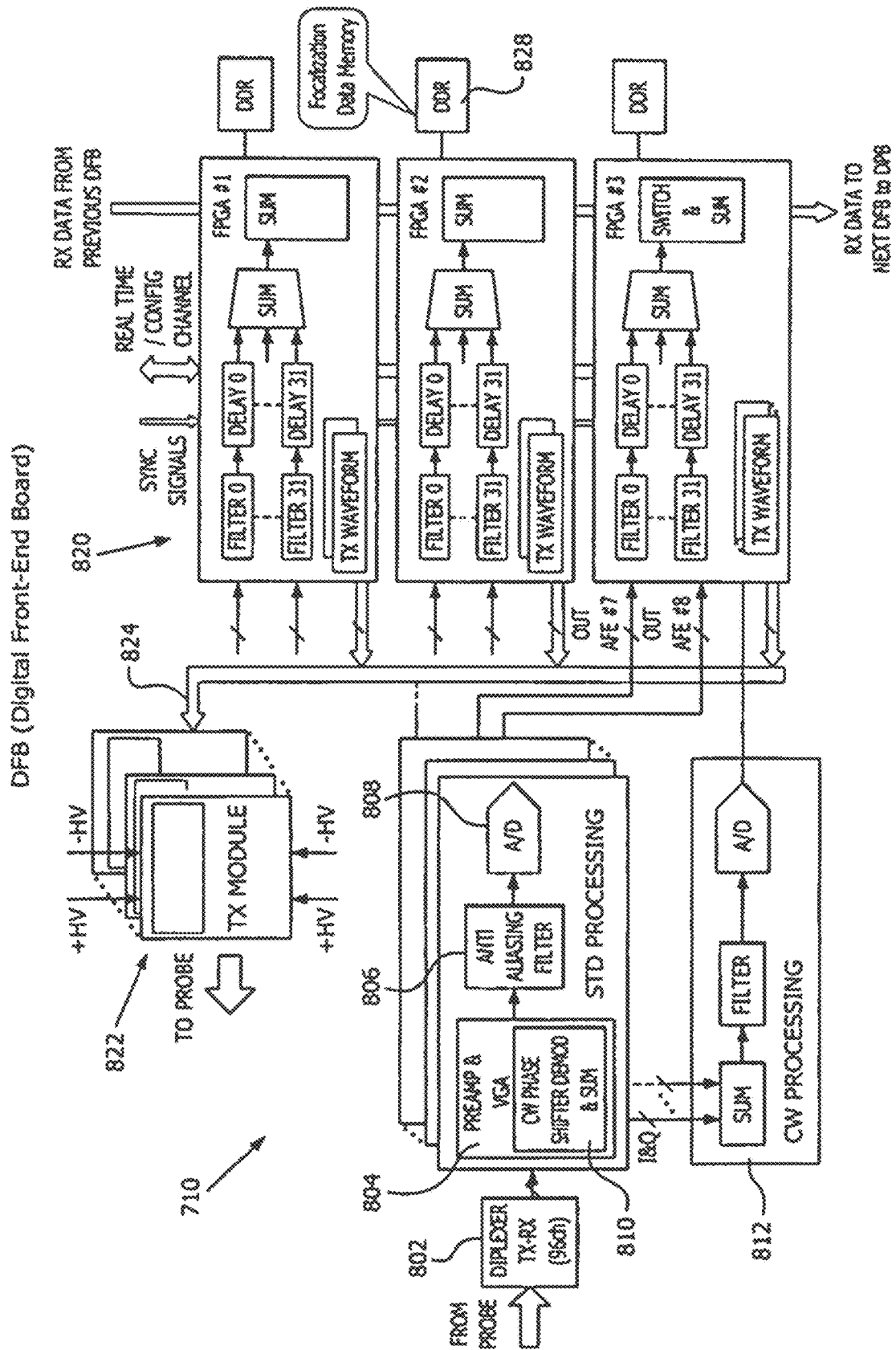
FIG. 8 illustrates a block diagram of a portion of the digital front-end boards.

FIG. 8 illustrates a block diagram of a portion of the digital front-end boards 710 formed in accordance with embodiments herein. A group of diplexers 802 receive the ultrasound signals for the individual channels over the PIB output 808. The ultrasound signals are passed along a standard processing circuit 805 or to a continuous wave processing circuit 812, based upon the type of probing utilized. When processed by the standard processing circuit 805, a preamplifier and variable gain amplifier 804 process the incoming ultrasound receive signals that are then provided to an anti-aliasing filter 806 which performs anti-aliasing filtering.

According to an embodiment the retrospective transmit beam focusing may be applied to the RF data directly acquired by the system or to transformed data according to different transformations as for example as a phase/quadrature (I/Q) transformation, or similar.

In the embodiment of FIG. 8 an example of the said transformation of the RF data is disclosed According to this example, the output of the filter 806 is provided to an A/D converter 808 that digitizes the incoming analog ultrasound receive signals. When a continuous wave (CW) probe is utilized, the signals therefrom are provided to a continuous wave phase shifter, demodulator and summer 810 which converts the analog RF receive signals to I,Q data pairs. The CW I,Q data pairs are summed, filtered and digitized by a continuous wave processing circuit 812. Outputs from the standard or continuous wave processing circuits 805, 812 are then passed to beam forming circuits 820 which utilize one or more FPGAs to perform filtering, delaying and summing the incoming digitized receive signals before passing the RF data to the digital processing board 826 (FIG. 7). The FPGAs receive focalization data from memories 828. The focalization data is utilized to manage the filters, delays and summing operations performed by the FPGAs in connection with beamforming. The beamformed RF or I/Q data is passed between the beamforming circuits 820 and ultimately to the digital processing board 726.

The digital front-end boards 710 also include transmit modules 822 that provide transmit drive signals to corresponding transducers of the ultrasound probe. The beamforming circuits 820 include memory that stores transmit waveforms. The transmit modules 822 receive transmit waveforms over line 824 from the beamforming circuits 820.

Figure 9:
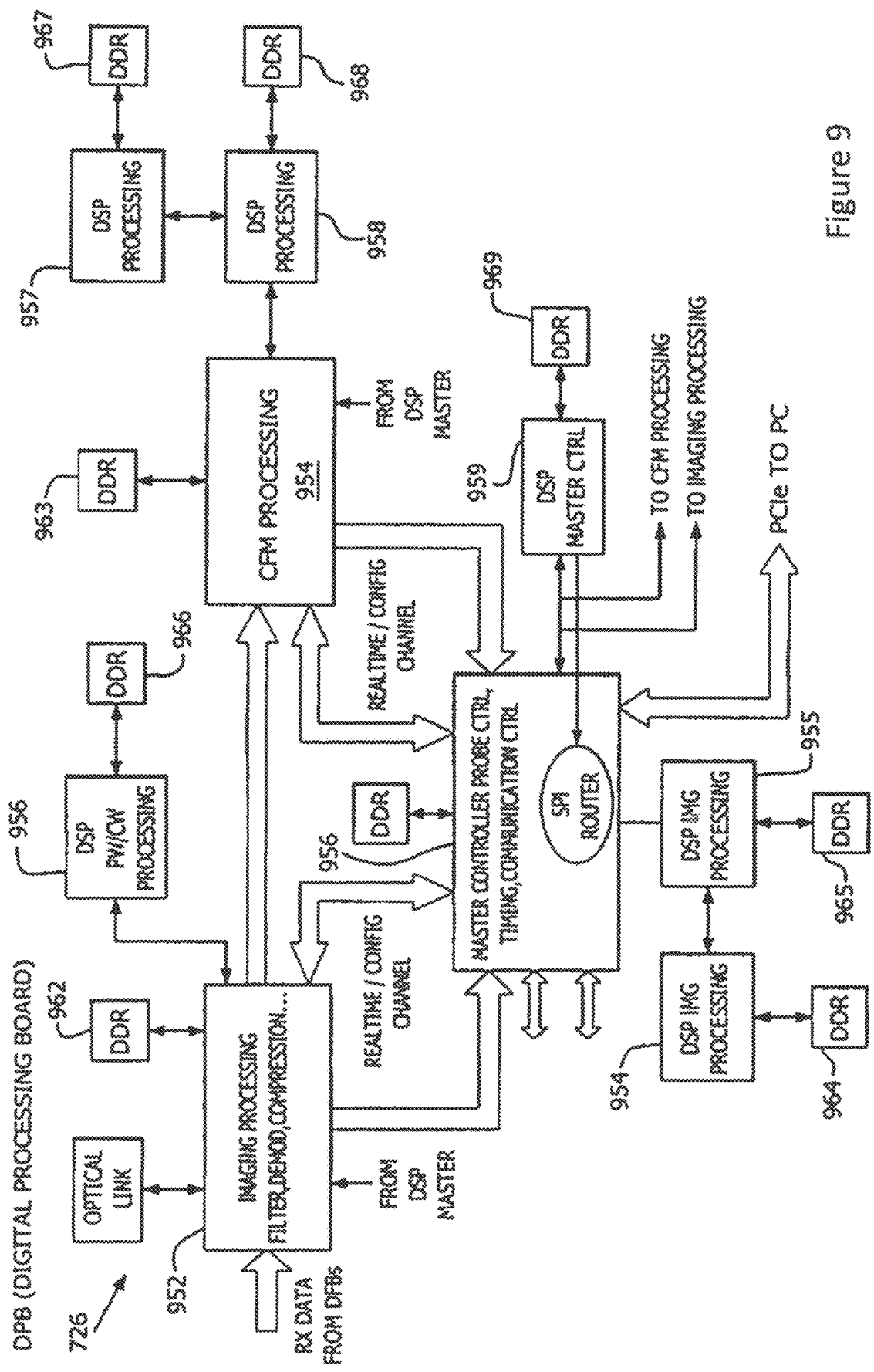
FIG. 9 illustrates a block diagram of the digital processing board.

FIG. 9 illustrates a block diagram of the digital processing board 726 implemented in accordance with embodiments herein. The digital processing board 726 includes various processors 952-959 to perform different operations under the control of program instructions saved within corresponding memories see 962-969. A master controller 950 manages operation of the digital processing board 726 and the processors 952-959. By way of example, one or more processors as the 952 may perform filtering, the modulation, compression and other operations, while another processor 953 performs colour flow processing. The master controller provides probe control signals, timing control signals, communications control and the like. The master controller 950 provides real-time configuration information and synchronization signals in connection with each channel to the digital front-end board 710.

It should be clearly understood that the various arrangements and processes broadly described and illustrated with respect to the figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

Aspects are described herein with reference to the figures, which illustrate example methods, devices and program products according to various example embodiments. These program instructions may be provided to a processor of a general-purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

One or more of the operations described above in connection with the methods may be performed using one or more processors. The different devices in the systems described herein may represent one or more processors, and two or more of these devices may include at least one of the same processors. In one embodiment, the operations described herein may represent actions performed when one or more processors (e.g., of the devices described herein) execute program instructions stored in memory (for example, software stored on a tangible and non-transitory computer readable storage medium, such as a computer hard drive, ROM, RAM, or the like).

The processor(s) may execute a set of instructions that are stored in one or more storage elements, in order to process data. The storage elements may also store data or other information as desired or needed. The storage element may be in the form of an information source or a physical memory element within the controllers and the controller device. The set of instructions may include various commands that instruct the controllers and the controller device to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

The controller may include any processor-based or microprocessor-based system including systems using microcontrollers, reduced instruction set computers (RISC), application specific integrated circuitry (ASICs), field-programmable gate arrays (FPGAs), logic circuitry, and any other circuit or processor capable of executing the functions described herein. When processor-based, the controller executes program instructions stored in memory to perform the corresponding operations. Additionally, or alternatively, the controllers and the controller device may represent circuitry that may be implemented as hardware. The above examples are exemplary only and are thus not intended to limit in any way the definition and/or meaning of the term "controller."

Optionally, aspects of the processes described herein may be performed over one or more networks one a network server. The network may support communications using any of a variety of commercially-available protocols, such as Transmission Control Protocol/Internet Protocol ("TCP/IP"), User Datagram Protocol ("UDP"), protocols operating in various layers of the Open System Interconnection ("OSI") model, File Transfer Protocol ("FTP"), Universal Plug and Play ("UpnP"), Network File System ("NFS"), Common Internet File System ("CIFS") and AppleTalk. The network can be, for example, a local area network, a wide-area network, a virtual private network, the Internet, an intranet, an extranet, a public switched telephone network, an infrared network, a wireless network, a satellite network and any combination thereof.

In embodiments utilizing a web server, the web server can run any of a variety of server or mid-tier applications, including Hypertext Transfer Protocol ("HTTP") servers, FTP servers, Common Gateway Interface ("CGI") servers, data servers, Java servers, Apache servers and business application servers. The server(s) also may be capable of executing programs or scripts in response to requests from user devices, such as by executing one or more web applications that may be implemented as one or more scripts or programs written in any programming language, such as Java®, C, C# or C++, or any scripting language, such as Ruby, PHP, Perl, Python or TCL, as well as combinations thereof. The server(s) may also include database servers, including without limitation those commercially available from Oracle®, Microsoft®, Sybase® and IBM® as well as open-source servers such as MySQL, Postgres, SQLite, MongoDB, and any other server capable of storing, retrieving and accessing structured or unstructured data. Database servers may include table-based servers, document-based servers, unstructured servers, relational servers, non-relational servers or combinations of these and/or other database servers.

The embodiments described herein may include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers or other network devices may be stored locally and/or remotely, as appropriate. Where a system includes computerized devices, each such device can include hardware elements that may be electrically coupled via a bus, the elements including, for example, at least one central processing unit ("CPU" or "processor"), at least one input device (e.g., a mouse, keyboard, controller, touch screen or keypad) and at least one output device (e.g., a display device, printer or speaker). Such a system may also include one or more storage devices, such as disk drives, optical storage devices and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.) and working memory as described above. The computer-readable storage media reader can be connected with, or configured to receive, a computer-readable storage medium, representing remote, local, fixed and/or removable storage devices as well as storage media for temporarily and/or more permanently containing, storing, transmitting and retrieving computer-readable information. The system and various devices also typically will include a number of software applications, modules, services or other elements located within at least one working memory device, including an operating system and application programs, such as a client application or web browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

Various embodiments may further include receiving, sending, or storing instructions and/or data implemented in accordance with the foregoing description upon a computer-readable medium. Storage media and computer readable media for containing code, or portions of code, can include any appropriate media known or used in the art, including storage media and communication media, such as, but not limited to, volatile and non-volatile, removable and non-removable media implemented in any method or technology for storage and/or transmission of information such as computer readable instructions, data structures, program modules or other data, including RAM, ROM, Electrically Erasable Programmable Read-Only Memory ("EEPROM"), flash memory or other memory technology, Compact Disc Read-Only Memory ("CD-ROM"), digital versatile disk (DVD) or other optical storage, magnetic cassettes, magnetic tape, magnetic disk storage or other magnetic storage devices or any other medium which can be used to store the desired information and which can be accessed by the system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the invention as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions and equivalents falling within the spirit and scope of the invention, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including" and "containing" are to be construed as open-ended terms (i.e., meaning "including, but not limited to,") unless otherwise noted. The term "connected," when unmodified and referring to physical connections, is to be construed as partly or wholly contained within, attached to or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. The use of the term "set" (e.g., "a set of items") or "subset" unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but the subset and the corresponding set may be equal.

Operations of processes described herein can be performed in any suitable order unless otherwise indicated herein or otherwise clearly contradicted by context. Processes described herein (or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

Preferred embodiments of this disclosure are described herein, including the best mode known to the inventors for carrying out the invention. Variations of those preferred embodiments may become apparent to those of ordinary skill in the art upon reading the foregoing description. The inventors expect skilled artisans to employ such variations as appropriate and the inventors intend for embodiments of the present disclosure to be practiced otherwise than as specifically described herein. Accordingly, the scope of the present disclosure includes all modifications and equivalents of the subject matter recited in the claims appended hereto as permitted by applicable law. Moreover, any combination of the above-described elements in all possible variations thereof is encompassed by the scope of the present disclosure unless otherwise indicated herein or otherwise clearly contradicted by context.

All references, including publications, patent applications and patents, cited herein are hereby incorporated by reference to the same extent as if each reference were individually and specifically indicated to be incorporated by reference and were set forth in its entirety herein.

The invention claimed is:

1. Method for shear wave elasticity imaging comprising:
   a) acquiring at least one B-mode ultrasound image of a target region in a body under examination;
   b) selecting a region of interest inside a B-mode image with anatomical structures of the at least one B-mode image;
   c) transmitting a shear wave excitation pulse focalized on an excitation region;
   d) measuring displacements of tissue in the body at different depths positions or at different depths ranges along each one of a predefined number of laterally staggered tracking lines within the selected region of interest and corresponding to a certain number of tracking focal points;
   e) determining a curve representing displacement of tissue as a function of time at different spatial locations within the region of interest;
   f) determining for each said spatial locations in the region of interest one or multiple candidate times of arrival of the shear wave at the spatial location as a function of the curve determined in step e);
   g) finding a linear functional relation between the time of arrival and the spatial coordinate in the lateral direction that is in the direction of propagation of the shear wave perpendicular to the direction of the tracking lines, which linear function best approximates the determined time of arrivals at the positions of the tracking lines along the lateral direction;
   h) determining the inverse of the velocity of the shear wave in a spatial location as an angular coefficient of the linear function in a coordinate system representing the time of arrival along the y-coordinate and the position along the lateral direction at which the time of arrival has been recorded on the x-coordinate, that is a slope of a straight line representing said linear function in the coordinate system;
   i) determining the elasticity parameters of the regions between at least two of the tracking focal points at the same depth and on at least two adjacent tracking lines as a function of the corresponding measured displacements caused by the shear wave at said at least two of the tracking focal points, and determining statistical reliability values for the elasticity parameters; and
   j) modifying the appearance of pixels of the B-mode image inside the region of interest and for which the velocity of the shear wave propagation and/or other elasticity parameters has been determined relatively to the B-mode image in grey scale as a function of the elasticity parameters determined for the pixels and displaying the pixels with a modified appearance at the corresponding pixels of the B-mode image to generate a combined image comprising the B-mode image with its anatomical structures and an elasticity image comprising the pixels with a modified appearance overlaid with a statistical reliability image comprising the statistical reliability values for the elasticity parameters used for corresponding ones of the pixels with a modified appearance;
   wherein step g) comprises determining the linear function best fitting the candidate times of arrival applying a Random Sample Consensus algorithm (RANSAC algorithm).

2. Method according to claim 1, wherein determining one or multiple candidate time of arrival of the shear wave for each different spatial coordinates or locations is carried out according to one of the following alternatives selected from:
   setting as the one candidate time of arrival of the shear wave the time of the peak of the displacement curve at the corresponding spatial location;
   setting as the multiple candidate times of arrival of the shear wave the time of the local maxima of the displacement curve at the corresponding spatial location;
   setting the one said candidate time of arrival of the shear wave at the different spatial coordinates using the peak of the cross-correlation between the measured displacement curve at a spatial location and a reference displacement curve, whereby the reference displacement curve is obtained by measuring a displacement curve at a reference lateral position or coordinate corresponding to an absolute time of peak or at the position of the line of sight which is laterally adjacent to a line of sight at which the time of arrival is to be determined corresponding to a relative time of peak or the reference curve is a synthetic one obtained from theory or by simulations; or
   setting said multiple candidate time of arrival of the shear wave at the different spatial coordinates using the local maxima of the cross-correlation between the measured displacement curve at a spatial location and a reference displacement curve, whereby the reference displacement curve is obtained by measuring a displacement curve at a reference lateral position or coordinate corresponding to an absolute time of peak or at the position of the line of sight which is laterally adjacent to the line of sight at which the time of arrival is to be determined corresponding to a relative time of peak or the reference curve is a synthetic one obtained from theory or by simulations.

3. Method according to claim 1, wherein the best fitting regression line is determined by considering one or a combination of criteria selected from a group comprising:
   a number of outliers in a set of the candidate times of arrival is minimum; and
   quadratic error of so-called inliers in the set of the candidate times is a minimum.

4. Method according to claim 1, wherein the spatial locations at which the time of arrival of the local maxima are determined are tracking points or depth ranges positioned at different depth on at least part or on each of the tracking lines crossing the region of interest.

5. Method according to claim 1, wherein the displacement curve as a function of time related to a tracking line that is at the corresponding lateral position of the tracking line relatively to the other tracking lines in the lateral direction is the average of the measured displacements at a plurality of tracking points on the tracking line having different depths or at a plurality of depth ranges along the tracking line having different depths.

6. Method according to claim 1, wherein the velocity of the shear wave is determined separately at least at two different depths of the region of interest by carrying out the steps a) to i) separately for each of the two depths.

7. Method according to claim 6, wherein for each of the two depths the displacement curves are determined at tracking points or at depth ranges positioned on the tracking lines at the at least two depths or representative of the depths, the steps a) to i) being carried out independently for the displacement curves as a function of time determined at the tracking line positions at each one of the at least two depths.

8. Method for shear wave elasticity imaging comprising:
   a) acquiring at least one B-mode ultrasound image of a target region in a body under examination;
   b) selecting a region of interest inside a B-mode image with anatomical structures of the at least one B-mode image;
   c) transmitting a shear wave excitation pulse focalized on an excitation region;
   d) measuring displacements of tissue in the body at different depths positions or at different depths ranges along each one of a predefined number of laterally staggered tracking lines within the selected region of interest and corresponding to a certain number of tracking focal points;
   e) determining a curve representing displacement of tissue as a function of time at different spatial locations within the region of interest;
   f) determining for each said spatial locations in the region of interest one or multiple candidate times of arrival of the shear wave at the spatial location by setting:
   as the one time of arrival of the shear wave the time of the peak of the displacement curve at the corresponding spatial location or the time of peak of the cross correlation of the measured displacement curve at the spatial location with a reference displacement curve measured at a reference spatial location or determined from theoretical calculations or simulations or
   as the multiple times of arrival, the times of local maxima of the displacement curve at the corresponding spatial location or the times of local maxima of the cross correlation of the measured displacement curve at the spatial location with a reference displacement curve measured at a reference spatial location or determined from theoretical calculations or simulations;
   g) finding a linear functional relation between the time of arrival and the spatial coordinate in the lateral direction that is in the direction of propagation of the shear wave perpendicular to the direction of the tracking lines, which linear function best approximates the determined time of arrivals at the positions of the tracking lines along the lateral direction;
   h) determining the inverse of the velocity of the shear wave in a spatial location as an angular coefficient of the linear function in a coordinate system representing the time of arrival along the y-coordinate and the position along the lateral direction at which the time of arrival has been recorded on the x-coordinate, that is a slope of a straight line representing the linear function in the coordinate system;
   i) estimating at one or more of the spatial locations that is at one or more of the lateral positions of the tracking lines, expected maximum and minimum values of the velocities of propagation of the shear wave at the spatial locations;
   j) mapping the values on the coordinate system representing the data pairs relating to the time of arrival of the maxima of the displacement curves and the corresponding position in the lateral direction that is the position of the corresponding tracking line; and
   k) not considering for the execution of step g) the data pairs relating to time of arrival and position of the corresponding tracking line corresponding to shear wave velocities which are higher than the maximum velocity or lower than the minimum velocity estimated in steps i) and j) at the position of the corresponding tracking line;
   l) determining the elasticity parameters of the regions between at least two of the tracking focal points at the same depth and on at least two adjacent tracking lines as a function of the corresponding measured displacements caused by the shear wave at said at least two of the tracking focal points, and determining statistical reliability values for the elasticity parameters; and
   m) modifying the appearance of pixels of the B-mode image inside the region of interest and for which the velocity of the shear wave propagation and/or other elasticity parameters has been determined relatively to the B-mode image in grey scale as a function of the elasticity parameters determined for the pixels and displaying the pixels with a modified appearance at the corresponding pixels of the B-mode image to generate a combined image comprising the B-mode image with its anatomical structures and an elasticity image comprising the pixels with a modified appearance overlaid with a statistical reliability image comprising the statistical reliability values for the elasticity parameters used for corresponding ones of the pixels with a modified appearance.

9. Method according to claim 8, wherein a time of start of the shear wave propagation is added to the data pairs relating to time of arrival and lateral position on which the step g) is carried out, and the time of start is optionally weighted higher than other data in the data pairs.

10. Method according to claim 8, wherein the velocity of the shear wave propagation is used as a basis for calculating elasticity parameters including one or more of the parameters of a group comprising: velocity of the shear wave propagation, Young's modulus, shear modulus, bulk modulus, Poisson's ratio, Lamè's first parameter, P-wave and combinations of these parameters.

11. Method for quantifying the elasticity of a material by ultrasounds comprising:
   a) acquiring an ultrasound image;
   b) defining a region of interest in the image;
   c) defining an excitation region or point in the acquired image;
   d) generating at least one acoustic excitation ultrasound pulse and transmitting the excitation ultrasound pulse focalized at the excitation region or point, for generating at least one shear wave, which shear wave originates in a first excitation point and has a direction of a propagation perpendicular to the direction of propagation of the ultrasound excitation pulse, the excitation region or point being positioned in such a manner that the shear wave passes through the region of interest;
   e) measuring displacements of tissue in the body induced by the shear wave in the region of interest at a plurality of tracking lines of sight passing through the region of interest and at different predetermined laterally staggered distances from the excitation region or point and within a predefined depth range along each tracking line that correspond to predefined tracking focal points;

f) calculating the speed of a measured shear wave using the displacement data at the tracking focal points;

g) assessing, by calculation, elasticity parameter values of the material in the region of interest based on measured speed of the shear wave;

h) measuring the displacements of a certain number of tracking focal points at different depths positions or at different depths ranges along each one of a predefined number of laterally staggered tracking lines within the selected region of interest;

i) determining the elasticity parameters of the regions between at least two of the tracking focal points at the same depth and on at least two adjacent tracking lines as a function of the corresponding measured displacements caused by the shear wave at said at least two of the tracking focal points, and determining statistical reliability values for the elasticity parameters; and j) modifying the appearance of pixels of a B-mode images with anatomical structures inside the region of interest and for which the velocity of the shear wave propagation and/or other elasticity parameters has been determined relatively to a the B-mode image in grey scale as a function of the elasticity parameters determined for the pixels and displaying the pixels with a modified appearance at the corresponding pixels of the B-mode image to generate a combined image comprising the B-mode image with its anatomical structures and an elasticity image comprising the pixels with a modified appearance overlaid with a statistical reliability image comprising the statistical reliability values for the elasticity parameters used for corresponding ones of the pixels with a modified appearance.

12. Method according to claim 11 in which step g) is carried out by applying the following steps:

g1) defining sub-regions of the region of interest which sub regions are delimited laterally by two of the tracking lines and in the direction of depth by depth ranges coinciding with at least one tracking point having a certain depth position on each of the two tracking lines and which at least one point or depth range on the first of the tracking line having equal depth as the corresponding at least one tracking point or depth range on the second tracking line;

g2) the two tracking lines and the depth ranges being directly adjacent one to the other or one or more tracking line and/or one or more tracking points or depth ranges being provided between the two tracking lines and the two tracking points or depth ranges;

g3) calculating the speed of the shear wave in each of the sub-regions of the region of interest using the displacement data at each tracking point or depth range on each tracking line delimiting and/or being within the sub-region; and g4) assessing, by calculation, an elasticity parameter of the material in each of the sub-regions of the region of interest based on the measured speed of the shear wave.

13. An ultrasound system for shear wave elasticity imaging (SWEI) comprising:
an ultrasound probe;
an ultrasound transmit-wave generator and an ultrasound transmit beamformer;
an ultrasound receive-beamformer;
ultrasound receive signals processing unit for generating ultrasound image data;
a shear wave excitation pulse generator and a shear wave beamformer;
a display;
a central control unit comprising:
a memory storing program instructions; and
at least one processor that executes the program instructions to:
define a region of interest in the ultrasound image;
generate an acoustic excitation ultrasound pulse directed at an excitation region or point, the acoustic excitation ultrasound pulse being configured to produce a shear wave that has a direction of propagation extending laterally from a direction of propagation of the acoustic excitation ultrasound pulse that is along a direction perpendicular to the direction of transmission of the ultrasound excitation pulse;
generate ultrasound tracking beams focused along different tracking lines which are at different predetermined laterally staggered distances one from the other and from the excitation region or point;
process the ultrasound echo signal reflected at different tracking focal points distributed along the tracking lines for calculating the values of elasticity parameters in the region of interest by:

a) measuring displacements of tissue in the body at different depths positions or at different depths ranges along each one of a predefined number of laterally staggered tracking lines within the selected region of interest and corresponding to a certain number of tracking focal points;

b) determining a curve representing displacement of tissue as a function of time at different spatial locations within the region of interest;

c) determining for each said spatial locations in the region of interest one or multiple candidate times of arrival of the shear wave at the spatial location by setting:
as the one time of arrival of the shear wave, the time of the peak of the displacement curve at the corresponding spatial location or the time of peak of the cross correlation of the measured displacement curve at the spatial location with a reference displacement curve measured at a reference spatial location or determined from theoretical calculations or simulations; or
as the multiple times of arrival, the times of the local maxima of the displacement curve at the corresponding spatial location or the times of the local maxima of the cross correlation of the measured displacement curve at the spatial location with a reference displacement curve measured at a reference spatial location or determined from theoretical calculations or simulations;

d) finding a linear functional relation between the time of arrival and the spatial coordinate in the lateral direction that is in the direction of propagation of the shear wave perpendicular to the direction of the tracking lines, which linear function best approximates the determined time of arrivals at the positions of the tracking lines along the lateral direction;

e) determining the inverse of the velocity of the shear wave in a spatial location as an angular coefficient of the linear function in a coordinate system representing the time of arrival along the y-coordinate and the position along the lateral direction at which the time of arrival has been recorded on the x-coordinate, that is a slope of a straight line representing the linear function in the coordinate system;

f) determining the elasticity parameters of the regions between at least two of the tracking focal points at the same depth and on at least two adjacent tracking lines as a function of the corresponding measured displacements caused by the shear wave at said at least two of the tracking focal points, and determining statistical reliability values for the elasticity parameters; and g) modifying the appearance of at least one pixel of a B-mode image with anatomical structures inside the region of interest and for which the velocity of the shear wave propagation and/or other elasticity parameters has been determined relatively to a the B-mode image in grey scale as a function of the elasticity parameters determined for the pixels and displaying the pixels with a modified appearance at the corresponding pixels of the B-mode image to generate a combined image comprising the B-mode image with its anatomical structures and an elasticity image comprising the pixels with a modified appearance overlaid with a statistical reliability image comprising the statistical reliability values for the elasticity parameters used for corresponding ones of the pixels with a modified appearance;

wherein step e) is carried out by determining the linear function best fitting the candidate times of arrival applying a Random Sample Consensus algorithm (RANSAC algorithm), the display configured to represent the elasticity parameters and/or velocity parameters value distribution in the region of interest by means of an elasticity image, the appearance of the pixels of the elasticity image being determined as a function of the elasticity parameter; and wherein the step g) comprises.

14. An ultrasound system for shear wave elasticity imaging (SWEI) comprising:
an ultrasound probe;
an ultrasound transmit-wave generator and an ultrasound transmit beamformer;
an ultrasound receive-beamformer;
ultrasound receive signals processing unit for generating ultrasound image data;
a shear wave excitation pulse generator and a shear wave beamformer;
a display;
a central control unit comprising:
a memory storing program instructions; and
at least one processor that executes the program instructions to:
define a region of interest in the ultrasound image;
generate an acoustic excitation ultrasound pulse directed at an excitation region or point, the acoustic excitation ultrasound pulse being configured to produce a shear wave that has a direction of propagation extending laterally from a direction of propagation of the acoustic excitation ultrasound pulse that is along a direction perpendicular to the direction of transmission of the ultrasound excitation pulse;
generate ultrasound tracking beams focused along different tracking lines which are at different predetermined laterally staggered distances one from the other and from the excitation region or point; and
process the ultrasound echo signal reflected at different tracking focal points distributed along the tracking lines for calculating the values of elasticity parameters in the region of interest by:

a) measuring displacements of tissue in the body at different depths positions or at different depths ranges along each one of a predefined number of laterally staggered tracking lines within the selected region of interest and corresponding to a certain number of tracking focal points;

b) determining a curve representing displacement of tissue as a function of time at different spatial locations within the region of interest;

c) determining for each said spatial locations in the region of interest one or multiple candidate times of arrival of the shear wave at the spatial location by setting, as the one time of arrival of the shear wave, the time of the peak of the displacement curve at the corresponding spatial location or the time of peak of the cross correlation of the measured displacement curve at the spatial location with a reference displacement curve measured at a reference spatial location or determined from theoretical calculations or simulations; or by setting as the multiple times of arrival, the times of the local maxima of the displacement curve at the corresponding spatial location, or the times of the local maxima of the cross correlation of the measured displacement curve at the spatial location with a reference displacement curve measured at a reference spatial location or determined from theoretical calculations or simulations;

d) finding a linear functional relation between the candidate times of arrival and the spatial coordinate in the lateral direction that is in the direction of propagation of the shear wave perpendicular to the direction of the tracking lines, which linear function best approximates the determined time of arrivals at the positions of the tracking lines along the lateral direction;

e) determining the inverse of the velocity of the shear wave in a spatial location as an angular coefficient of the linear function in a coordinate system representing the time of arrival along the y-coordinate and the position along the lateral direction at which the time of arrival has been recorded on the x-coordinate, that is a slope of a straight line representing the linear function in the coordinate system;

f) estimating at one or more of the spatial locations that is at one or more of the lateral positions of the tracking lines, expected maximum and minimum values of the velocities of propagation of the shear wave at the spatial locations;

g) mapping the values on the coordinate system representing the data pairs relating to the time of arrival of the maxima of the displacement curves and the corresponding position in the lateral direction that is the position of the corresponding tracking line;

h) not considering for the execution of step d) the data pairs relating to time of arrival and position of the corresponding tracking line corresponding to shear wave velocities which are higher than the maximum velocity or lower than the minimum velocity estimated in steps f) and g) at the position of the corresponding tracking line;

i) determining the elasticity parameters of the regions between at least two of the tracking focal points at the same depth and on at least two adjacent tracking lines as a function of the corresponding measured displacements caused by the shear wave at said at least two of the tracking focal points, and determining statistical reliability values for the elasticity parameters; and j) modifying the appearance of pixels of a B-mode image with anatomical structures inside the region of interest and for which the velocity of the shear wave propagation and/or other elasticity parameters has been determined relatively to a the B-mode image in grey scale as a function of the elasticity parameters determined for pixels and displaying the pixels with a modified appearance at the corresponding pixels of the B-mode image to generate a combined image comprising the B-mode image with its anatomical structures and an elasticity image comprising the pixels with a modified appearance overlaid with a statistical reliability image comprising the statistical reliability values for the elasticity parameters used for corresponding ones of the pixels with a modified appearance;

wherein the display is configured to represent the elasticity parameters and/or velocity parameters value distribution in the region of interest by means of an elasticity image, the appearance of the pixels of the elasticity image being determined as a function of the elasticity parameter.

15. An ultrasound system for shear wave elasticity imaging (SWEI) comprising:
   an ultrasound probe;
   an ultrasound transmit-wave generator and an ultrasound transmit beamformer;
   an ultrasound receive-beamformer;
   ultrasound receive signals processing unit for generating ultrasound image data;
   a shear wave excitation pulse generator and a shear wave beamformer;
   a display;
   a central control unit comprising:
   a memory storing program instructions; and
   at least one processor that executes the program instructions to:
   define a region of interest in the ultrasound image;
   generate an acoustic excitation ultrasound pulse directed at an excitation region or point, the acoustic excitation ultrasound pulse being configured to produce a shear wave that has a direction of propagation extending laterally from a direction of propagation of the acoustic excitation ultrasound pulse that is along a direction perpendicular to the direction of transmission of the ultrasound excitation pulse;
   generate ultrasound tracking beams focused along different tracking lines which are at different predetermined laterally staggered distances one from the other and from the excitation region or point; and
   process the ultrasound echo signal reflected at different tracking focal points distributed along the tracking lines for calculating the values of elasticity parameters in the region of interest by:
   e) measuring displacements induced by the shear wave at predefined tracking focal points in the region of interest at a plurality of tracking lines of sight passing through the region of interest and at different predetermined laterally staggered distances from the excitation region or point and within a predefined depth range along each tracking line;
   f) calculating the speed of a measured shear wave using the displacement data at the tracking focal points;
   g) assessing, by calculation, elasticity parameter values of the material in the region of interest based on a measured speed of the shear wave;
   h) measuring the displacements of tissue in the body at different depths positions or at different depths ranges along each one of a predefined number of laterally staggered tracking lines within the selected region of interest and corresponding to a certain number of tracking focal points;
   i) determining the elasticity parameters of the regions between at least two of the tracking focal points at the same depth and on at least two adjacent tracking lines as a function of the corresponding measured displacements caused by the shear wave at said at least two of the tracking focal points, and determining statistical reliability values for the elasticity parameters; and
   j) modifying the appearance of pixels of a B-mode image with anatomical structures inside the region of interest and for which the velocity of the shear wave propagation and/or other elasticity parameters has been determined relatively to a the B-mode image in grey scale as a function of the elasticity parameters determined for the pixels and displaying the pixels with a modified appearance at the corresponding pixels of the B-mode image to generate a combined image comprising the B-mode image with its anatomical structures and an elasticity image comprising the pixels with a modified appearance overlaid with a statistical reliability image comprising the statistical reliability values for the elasticity parameters used for corresponding ones of the pixels with a modified appearance;

wherein step g) comprises:
g1) defining sub-regions of the region of interest which sub regions are delimited laterally by two of the tracking lines and in the direction of depth by depth ranges coinciding with at least one tracking point having a certain depth position on each of the two tracking lines and which at least one point or depth range on the first of the tracking line having equal depth as the corresponding at least one tracking point or depth range on the second tracking line;
g2) the two tracking lines and the depth ranges being directly adjacent one to the other or one or more tracking line and/or one or more tracking points or depth ranges being provided between the two tracking lines and the two tracking points or depth ranges;
g3) calculating the speed of the shear wave in each of the sub-regions of the region of interest using the displacement data at each tracking point or depth range on each tracking line delimiting and/or being within the sub-region; and
g4) assessing, by calculation, an elasticity parameter of the material in each of the sub-regions of the region of interest based on the measured speed of the shear wave; and
wherein the display is configured to represent the elasticity parameters and/or velocity parameters value distribution in the region of interest by means of an elasticity image, the appearance of the pixels of the elasticity image being determined as a function of the elasticity parameter.

* * * * *